(12) United States Patent
Ogawa et al.

(10) Patent No.: US 7,790,773 B2
(45) Date of Patent: *Sep. 7, 2010

(54) CARBA-SUGAR AMINE DERIVATIVE AND GLYCOLIPID METABOLIC DISORDER TREATING AGENT CONTAINING THE SAME AS ACTIVE INGREDIENT

(75) Inventors: Seiichiro Ogawa, Tokyo (JP); Yoshiyuki Suzuki, Tokyo (JP); Eiji Nanba, Tottori (JP); Junichiro Matsuda, Tokyo (JP); Kousaku Ohno, Tottori (JP)

(73) Assignee: Seikagaku Corporation, Tokyo (JP)

( * ) Notice: Subject to any disclaimer, the term of this patent is extended or adjusted under 35 U.S.C. 154(b) by 729 days.

This patent is subject to a terminal disclaimer.

(21) Appl. No.: 10/793,857

(22) Filed: Mar. 8, 2004

(65) Prior Publication Data

US 2004/0225015 A1  Nov. 11, 2004

Related U.S. Application Data

(63) Continuation-in-part of application No. PCT/JP02/08882, filed on Sep. 2, 2002.

(30) Foreign Application Priority Data

Sep. 7, 2001  (JP)  ............................. 2001-272775
Sep. 7, 2001  (JP)  ............................. 2001-272776
Sep. 7, 2001  (JP)  ............................. 2001-272777

(51) Int. Cl.
  *A61K 31/133* (2006.01)
  *C07C 211/40* (2006.01)
  *C07C 215/44* (2006.01)

(52) U.S. Cl. ..................... 514/663; 514/671; 564/1; 564/462; 564/507; 564/509

(58) Field of Classification Search ............... 514/613, 514/625; 554/42
  See application file for complete search history.

(56) References Cited

U.S. PATENT DOCUMENTS

| 5,861,520 | A * | 1/1999 | Ogawa et al. ........... 554/42 |
| 6,274,597 | B1 | 8/2001 | Fan et al. |
| 6,583,158 | B1 | 6/2003 | Fan et al. |
| 6,589,964 | B2 | 7/2003 | Fan et al. |
| 6,599,919 | B2 | 7/2003 | Fan et al. |
| 6,774,135 | B2 | 8/2004 | Fan et al. |
| 6,916,829 | B2 | 7/2005 | Fan et al. |
| 7,141,582 | B2 | 11/2006 | Fan et al. |
| 7,514,453 | B2 | 4/2007 | Fan et al. |
| 7,485,755 | B2 * | 2/2009 | Suzuki et al. ........... 564/462 |
| 2004/0242539 | A1 | 12/2004 | Fan et al. |
| 2007/0021381 | A1 | 1/2007 | Fan et al. |

FOREIGN PATENT DOCUMENTS

EP  0049981 A1  4/1982
JP  2-237938  9/1990

OTHER PUBLICATIONS

Schiffmann et al., "New Prospects for the Treatment of Lysosomal Storage Diseases" Drugs (2002) vol. 62 No. 5 pp. 733-742.*
Database Chemical Abstracts [online], Seiichiro Ogawa, et al., "Synthetic studies on the validamycins. VI. Sythesis of DL-6'-epivalidoxylamine A", Database accession No. 98:89783, XP-002395824, 1982, 2 pages.
Jian-Qiang Fan, et al., "Accelerated transport and maturation of lysosomal α-galactosidase A in Fabry lymphoblasts by an enzyme Inhibitor", Nature Medicine, vol. 5, No. 1, XP-002293424, Jan. 1999, pp. 112-115.
Seiichiro Ogawa, et al., "Chemical Modification of the β-Glucocerebrosidase Inhibitor N-Octyl-β-vallenamine: Synthesis and Biological Evaluation of 4-Epimeric and 4-O-(β-$_D$-Galactipyranosyl) Derivatives", Bioorganic & Medicinal Chemistry, vol. 10, No. 6, 2002, pp. 1967-1972.
Seiichiro Ogawa, et al., "Synthesis of Potent β-D-Glucocerebrosidase Inhibitors: N-Alkyl-β-Valienamines", Bioorganic & Medicinal Chemistry Letters, vol. 6, No. 8, 1996, pp. 929-932.
Seiichiro Ogawa, et al., "Chemical Modification of β-Glucocerebrosidase Inhibitor N-Octyl-β-valienamine: Synthesis and Biological Evaluation of N-Alkanoyl and N-Alkyl Derivatives", Bioorganic & Medicinal Chemistry, vol. 6, No. 10, 1998, pp. 1955-1962.
Yukihiko Kameda, et al., "N-Substituted Valienamines, α-Glucosidase Inhibitors", The Journal of Antibiotics, vol. 35, No. 11, 1982, pp. 1624-1626.

* cited by examiner

Primary Examiner—Eric S Olson
(74) Attorney, Agent, or Firm—Oblon, Spivak, McClelland, Maier & Neustadt, L.L.P.

(57) ABSTRACT

A carba-sugar amine derivative represented by the following formula (1) or (2) is used as the active ingredient of a β-galactosidase inhibitor or a glycolipid metabolic disorder treating agent.

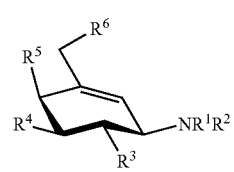

(1)

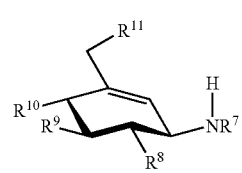

(2)

Wherein each of $R^1$ and $R^2$ independently represents H, an alkyl group, an acyl group, an aryl group or an aralkyl group, with the proviso that both are not H at the same time, and each of $R^3$, $R^4$, $R^5$ and $R^6$ independently represents a hydroxyl group or hydroxyl group having a substituent.

Also, $R^7$ represents an alkyl group, and each of $R^8$, $R^9$, $R^{10}$ and $R^{11}$ independently represents a hydroxyl group or a hydroxyl group having a substituent.

7 Claims, 14 Drawing Sheets

Compound 14

Compound 16

Compound 17

Compound 18

Compound 18

Substance 17 of the present invention

Substance 18 of the present invention

Concentration of substance (7) to be tested

Concentration of substance (7) to be tested

Concentration of substance (7) to be tested

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
tgggtgcgta actttgtcga                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2
cttagaggag cggtttagca                                          20
```

CARBA-SUGAR AMINE DERIVATIVE AND GLYCOLIPID METABOLIC DISORDER TREATING AGENT CONTAINING THE SAME AS ACTIVE INGREDIENT

CROSS-REFERENCE TO RELATED APPLICATIONS

The present application is a continuation-in-part of PCT/JP02/08882 filed on Sep. 2, 2002, which claims priority to JP 2001-272775, filed on Sep. 7, 2001, JP 2001-272776, filed on Sep. 7, 2001, and JP 2001-272777, filed on Sep. 7, 2001.

TECHNICAL FIELD

This invention relates to a pseudo-sugar having β-galactosidase inhibitory activity and a glycolipid metabolic disorder treating agent containing the substance or a pseudo-sugar having β-glucosidase inhibitory activity as the active ingredient.

BACKGROUND OF THE INVENTION

As glycolipid metabolic disorders, $G_{M1}$ gangliosidosis, Morquio-B disease, Krabbe's disease, Fabry's disease, Gaucher's disease, Tay-Sachs disease, Sandhoff disease, fucosidosis and the like are conventionally known. These diseases are those caused by the result of mutation of various glycolytic enzymes. Among them, $G_{M1}$ gangliosidosis, Morquio-B disease and Krabbe's disease are diseases caused by the loss of the enzyme activity of β-galactosidase due to its mutation, and Gaucher's disease is a disease caused by the loss of the activity of β-glucosidase due to its mutation. However, medicaments effective for these diseases have not been developed yet.

By the way, Fabry's disease is a disease caused by the mutation of α-galactosidase, and it is known that an α-galactosidase inhibitor could become a therapeutic drug of this disease (*Nature Medicine*, 5(1), 112-115 (1999)). It is considered that the aforementioned enzyme inhibitor recovers the enzyme activity by a mechanism in which the strong enzyme inhibitor stabilizes a mutant enzyme protein expressed in cells at a low concentration.

In the case that an enzyme inhibitor can stabilize a mutant enzyme protein, it is highly possible that a β-galactosidase inhibitor is effective as a therapeutic drug for diseases induced by the mutation of β-galactosidase, and it is highly possible also that a β-glucosidase inhibitor is effective as a therapeutic drug for diseases induced by the mutation of β-glucosidase.

However, a β-galactosidase inhibitor or β-glucosidase inhibitor which specifically and strongly inhibits human β-galactosidase or β-glucosidase has not been obtained so that the aforementioned therapeutic drug has not been developed yet.

DISCLOSURE OF THE INVENTION

Taking the aforementioned problems into consideration, the present inventors have conducted intensive studies on the screening and evaluation of sugar analogs capable of specifically inhibiting β-galactosidase activity and found as a result that specific carba-sugar amine derivatives show high β-galactosidase inhibitory activity. Thereafter, we have found that the carba-sugar amine derivatives regenerate enzyme activity of a human β-galactosidase mutant which reduced or lost the enzyme activity by a genetic mutation. We have found also that specific carba-sugar amine derivatives show high β-glucosidase inhibitory activity and that the carba-sugar amine derivatives regenerate enzyme activity of a human β-glucosidase mutant which reduced or lost the enzyme activity by a genetic mutation.

Accordingly, a first gist of the present invention relates to a carba-sugar amine derivative represented by the following formula (1):

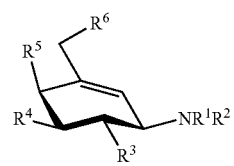

(1)

wherein each of $R^1$ and $R^2$ independently represents H, an alkyl group, an alkenyl group, an alkynyl group, an acyl group, an aryl group or an aralkyl group, wherein both are not H at the same time; and wherein each of $R^3$, $R^4$, $R^5$ and $R^6$ independently represents a hydroxyl group or a hydroxyl group having a substituent.

Also, a second gist of the present invention relates to an agent for treating a glycolipid metabolic disorder which comprises the aforementioned carba-sugar amine derivative as an active ingredient.

In addition, a third gist of the present invention relates to an agent for treating a glycolipid metabolic disorder which comprises a carba-sugar amine derivative represented by the following formula (2) as an active ingredient:

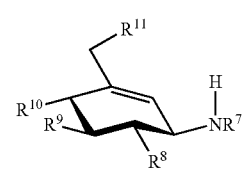

(2)

wherein $R^7$ represents an alkyl group, and each of $R^8$, $R^9$, $R^{10}$ and $R^{11}$ independently represents a hydroxyl group or a hydroxyl group having a substituent.

The present invention is further described below in detail based on the embodiments of the present invention.

(1) Substance of the Present Invention

The substance of the present invention is a carba-sugar amine derivative represented by the aforementioned formula (1).

In this case, each of $R^1$ and $R^2$ independently represents a functional group which is used for the modification or protection of amino group such as H, an alkyl group, an aryl group, or an aralkyl group. However, it is particularly desirable that one of $R^1$ and $R^2$ is an alkyl group and the other is H.

Examples of the aforementioned alkyl group include straight or branched chain alkyl groups having from 1 to 23, preferably from 2 to 20, carbon atoms. Particularly, when used as a galactosidase inhibitor considered to be desirable as an agent for treating sphingoglycolipid metabolic disorders, it is desirable that the substance of the present invention can become an analog of a sphingoglycolipid. That is, as an analog of a sphingoglycolipid mainly existing in the living body, it is most desirable that $R^1$ in the aforementioned formula of the substance of the present invention particularly has a straight chain alkyl group having from 2 to 18 carbon atoms.

Also, the alkyl group may be an alkoxyalkyl group having an alkyl glycerol-derived backbone as shown by the following formula (3) or an acyloxyalkyl group having an acyl glycerol-derived backbone (in the following structural formula, each of l and m is independently an integer of from 0 to 18, each of X independently represents a methylene group or a carbonyl group).

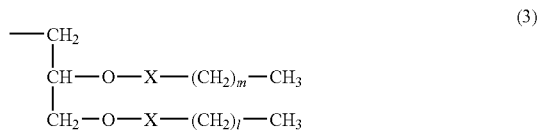

(3)

It is desirable that each of the aforementioned alkenyl group and alkynyl group has from 1 to 23, preferably from 2 to 22, carbon atoms, and may have two or more of a carbon-to-carbon double bond or triple bond. However, those in which two or more hydrogen atoms bound to these carbon atoms are replaced with an amino group, an amino group having a substituent, a hydroxyl group or a hydroxyl group having a substituent are not desirable, because the synthesis process becomes complex.

The aforementioned acyl group may be any group generally represented by —CO—R, but the number of carbon atoms is from 1 to 23, preferably from 2 to 20, based on the entire acyl group. In this connection, R in the aforementioned formula is a group selected from the aforementioned alkyl group, alkenyl group and alkynyl group or the aryl group and aralkyl group described below.

In addition, examples of the aforementioned aryl group include aromatic hydrocarbon residues such as a phenyl group and a naphthyl group or these aromatic groups further substituted with a substituent such as an alkyl group and an acyl group (e.g., tolyl group and the like).

The aforementioned aralkyl group is a functional group having a general structure of Ar—(CH$_2$)— in which an alkyl group is bound to the aforementioned aryl group (Ar), wherein the aforementioned n is preferably from 1 to 20, more preferably from 2 to 18. Examples of the aralkyl group include a benzyl group, a phenethyl group, an α-methylbenzyl group and the like.

Each of $R^3$, $R^4$, $R^5$ and $R^6$ represents a hydroxyl group or a hydroxyl group having a substituent. Among these, a hydroxyl group is particularly desirable. In this case, although it is not particularly limited, examples of the substituent group include aralkyl groups (benzyl group, phenethyl group, α-methylbenzyl group and the like), silyl groups (trimethylsilyl group, triethylsilyl group, triisopropylsilyl (TIPS) group, t-butyldiphenylsilyl (TBDPS) group, t-butyldimethylsilyl (TBDMS) group and the like), alkanoyl groups (acetyl group, butyryl group and the like), aroyl groups (benzoyl group, toluoyl group, naphthoyl group and the like), alkoxyalkyl groups (methoxymethyl (MOM) group and the like) and aralkyloxyalkyl groups (benzyloxymethyl (BOM) group and the like). Among these, MOM group is particularly desirable from the viewpoint of its stability and easy handling and elimination.

In this connection, since the substance of the present invention is a kind of pseudo-sugar, provision of carbon numbers is described herein by the method shown in the following structural formula (4) in accordance with the case of hexose.

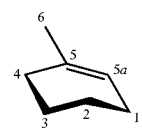

(4)

Also, since the substance of the present invention can be regarded as a (5-5a) unsaturated derivative of 5a-carba-D-hexopyranose, it is β type when the substituted amino group represented by $NR^1R^2$ in the formula (1) is positioned upper side of the six-membered ring, or a type when it is on the opposite side, so that the substance of the present invention is β type.

Accordingly, the most preferred substance among the substances of the present invention is the substance represented by the following structural formula (5):

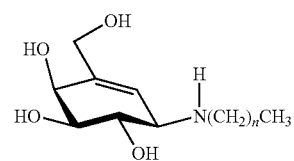

(5)

wherein n=0-22.

Since the substance of the present invention has high inhibitory activity upon β-galactosidase derived from a mammal, particularly human, it is possible to use it as a reagent for inhibiting such an enzyme in vitro or in vivo (in a cell, tissue or the like) and as a medicament based on such an enzyme inhibitory activity. Furthermore, it can be used in the studies on pathology of diseases induced by the mutation of β-galactosidase, and it can also be used as the active ingredient of a glycolipid metabolic disorder treating agent which will be described later.

In this connection, it is possible to calculate the inhibitory activity upon β-galactosidase, by adding the substance of the present invention to a solution containing β-galactosidase and its substrate and comparing the enzyme activity with that in the case where the substance of the present invention is not added.

It is desirable that the substance of the present invention has a 50% inhibition concentration ($IC_{50}$) of less than 1 µM based on the activity of human β-galactosidase, and it is particularly desirable that its $IC_{50}$ is less than 0.5 µM.

The substance of the present invention can be prepared using a well known substance di-O-isopropylidene-β-varienamine (*Bioorganic & Medicinal Chemistry Letters*, 6 (1996), 929-932: the following formula (6)) (cf. FIG. 1).

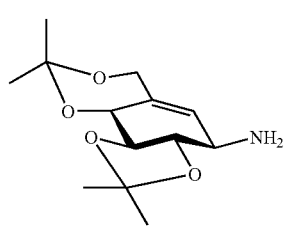

(6)

For example, as shown in FIG. 1, a compound 2 is obtained by acylating the amino group of di-O-isopropylidene-β-varienamine with an activated acyl group such as an acid chloride represented by a formula R$^{1'}$—COCl. This is converted into a compound 3 by reducing the amide bond of the compound 2 with lithium aluminum hydride, further converted into a compound 9 by protecting its hydroxyl group and amino group with an appropriate protecting group, so that it can withstand the reaction conditions for converting the 4-position hydroxyl group from a glucose type conformation to a galactose type configuration, and then converted into a ketone form (compound 10) by oxidizing the 4-position hydroxyl group, and the substance 1 of the present invention (the following formula (7): —CH$_2$—R$^1$ corresponds to —R$^{1'}$ except acyl group and —CO—R$^{2'}$ corresponds to an acyl group —R$^2$, the same shall apply hereinafter) is obtained by further reducing the carbonyl group. A substance 2 of the present invention (the following formula (8)) can be obtained by deprotecting the substance 1 of the present invention, and a substance 4 of the present invention (the following formula (10)) can be obtained by reducing the amide bond of the substance 1 of the present invention to convert it into a substance 3 of the present invention (the following formula (9)) and then deprotecting the latter (cf. FIG. 1).

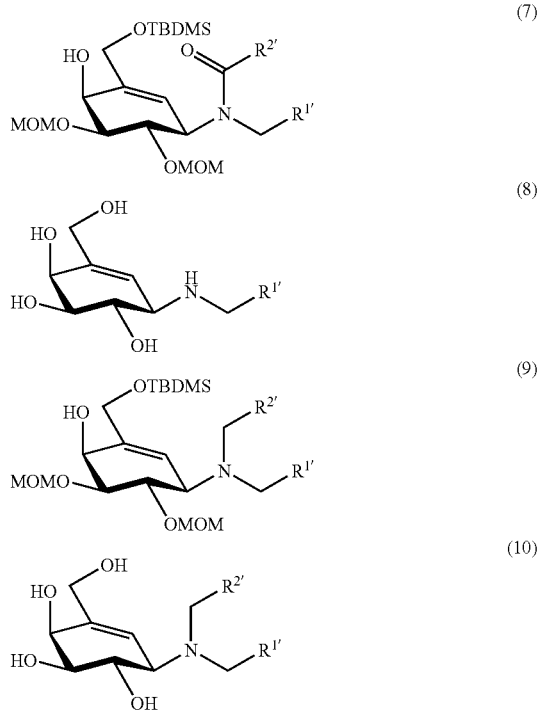

The aforementioned acylation, reduction by lithium aluminum hydride, conversion of a protecting group, oxidation of a hydroxyl group, reduction of a carbonyl group and deprotection can be easily carried out by those skilled in the art.

Specifically, acylation is carried out by allowing an activated acyl group such as an acid chloride represented by a formula R—COCl or an acylation agent such as an acid anhydride represented by R$^{1'}$—CO—O—CO—R$^{1'}$ to react with a material amine in basic organic solvent such as pyridine. The reaction may also be carried out as the reaction solvent using an inert solvent such as dichloromethane instead of pyridine and in the presence of a base such as triethylamine. The reaction is generally carried out at a temperature of from ice-cooling to room temperature, but the system may be heated to about 60° C., if necessary. The reaction time is approximately from 20 minutes to 20 hours but is preferably from 1 to 2 hours. The reduction by lithium aluminum hydride is carried out usually in an anhydrous organic solvent such as tetrahydrofuran. The reaction temperature is preferably from ice-cooling to room temperature, but the reaction may be carried out under reflux, if necessary. The reaction time is approximately from 30 minutes to 24 hours but is preferably about 2 hours.

As the protecting group, it may be any protecting group, so long as it can be oxidation of the 4-position hydroxyl group and subsequent by reducing a carbonyl group, but TBDMS group, MOM group and the like can be used from the viewpoint of easy handling and easy elimination. Examples of the conversion of the protecting group are described with reference to FIG. 1. N-Substituted-N-tert-butoxycarbonyl-1-deoxy-2,3:4,6-di-O-isopropylidene-5a-carba-β-D-xylo-hexo-5(5a)-enopyranosylamine (compound 4) can be obtained by reacting the compound 3 with di-tert-butyl dicarbonate in the presence of triethylamine, to protect the amino group with a butoxycarbonyl group. The compound 4 forms cyclic structures at the 2,3-positions and the 4,5-positions, and it is possible to obtain N-substituted-N-tert-butoxycarbonyl-1-deoxy-5a-carba-O-D-xylo-hexo-5(5a)-enopyranosylamine (compound 5), in which these cyclic structures are cleaved, by treating the compound 4 with weak acid such as acetic acid.

N-Substituted-N-tert-butoxycarbonyl-2,3-di-O-methoxymethyl-5a-carba-β-D-xylo-hexo-5(5a)-enopyranosylamine (compound 8) can be obtained by reacting α,α-dimethoxytoluene and p-toluenesulfonic acid monohydrate with the compound 5 to obtain benzylidene-added N-substituted-N-tert-butoxycarbonyl-4,6-O-benzylidene-5a-carba-β-D-xylo-hexo-5(5a)-enopyranosylamine (compound 6), reacting the 2-position and 3-position hydroxyl groups of the compound 6, for example, with 1,2-chloromethyl ether and N,N-diisopropylethylamine, to bind to a methoxymethyl (MOM) group as a protecting group to obtain N-substituted-N-tert-butoxycarbonyl-4,6-O-benzylidene-2,3-di-O-methoxymethyl-5a-carba-β-D-xylo-hexo-5(5a)-enopyranosylamine (compound 7), and then cleaving the benzylidene ring at the 4,5,6-positions using weak acid such as aqueous acetic acid.

N-Substituted-N-tert-butoxycarbonyl-2,3-di-O-methoxymethyl-6-O-tert-butyldimethylsilyl-5a-carba-β-D-xylo-hexo-5(5a)-enopyranosylamine (compound 9) can be obtained by reacting the compound 8 with imidazole and tert-butylchlorodimethylsilane to convert the 6-position hydroxyl group into a tert-butyldimethylsilyl group.

Furthermore, the most desirable substance of the present invention, N-substituted-5a-carba-α-L-arabino-hexo-5(5a)-enopyranosylamine (substance 2 of the present invention in FIG. 1 or substance 18 of the present invention in FIG. 6; the following formula 12), can be obtained by firstly obtaining N-substituted-N-tert-butoxycarbonyl-2,3-di-O-methoxymethyl-6-O-tert-butyldimethylsilyl-5a-carba-α-L-arabino-hexo-5(5a)-enopyranosylamine (substance 1 of the present invention in FIG. 1 or substance 17 of the present invention in FIG. 6; the following formula 11) in which a galacto type conformation was formed by treating the 4-position hydroxyl group of the compound 9 with an oxidizing agent such as pyridinium chlorochromate and then reducing it with a reducing agent such as tri-sec-butyl borohydride to invert the 4-position hydroxyl group, and then removing the tert-butyldimethylsilyl group as a 6-position hydroxyl group-protecting group and the butyloxycarbonyl group as a protecting group bound to the 1-position amino group by a treatment with strong acid such as hydrochloric acid.

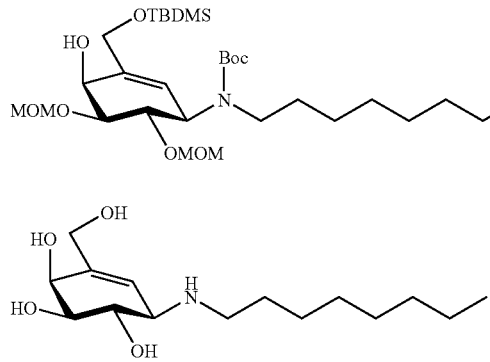

Also, the substance 2 of the present invention can be obtained using a compound described in JP-A-8-48658, 1-amino-6-O-(t-butyldimethylsilyl)-5a-carba-1-deoxy-2,3-dimethoxymethyl-α-L-arabino-hexo-5-enopyranose (compound 11 shown in FIG. 2 and FIG. 3), as the starting material, by acylating the material to obtain a compound 5 of the present invention (the following formula (13)) and further reducing it with lithium aluminum hydride, followed by deprotection in the same manner as described in the above (FIG. 2). Also, the substance 4 of the present invention can be obtained using the substance 7 of the present invention as the material, via the substance 8 of the present invention and the substance 3 of the present invention in that order, followed by acylation, reduction by lithium aluminum hydride and deprotection in successive combination.

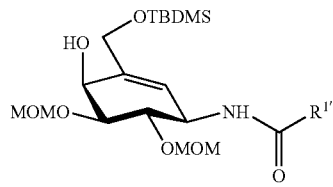

Also, a compound 6 of the present invention (the following formula (14)) which is an acyl derivative can be obtained by deprotecting the compound 5 of the present invention under acidic conditions, and a compound 9 of the present invention (the following formula (6)) can be obtained by treating a compound 8 of the present invention (an acyl derivative: the following formula (15)) in the same manner.

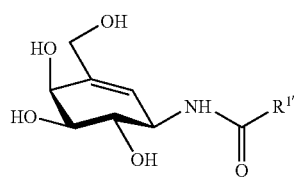

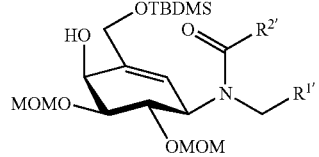

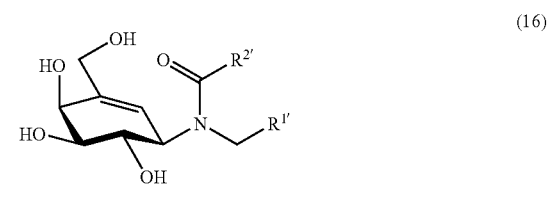

Also, a compound 12 of the present invention (the following formula (18)) can be obtained by reacting the amino group of a material compound (e.g., compound 11) with an alkyl halide represented by a formula $R^1$—Z (wherein $R^1$ is the same as the alkyl group of formula (1), and Z represents a halogen atom or an activation group such as mesyloxy group and tosyloxy group) or an alkyl derivative having an activation group such as mesyloxy group and tosyloxy group, instead of its acylation with an acid chloride represented by a formula $R^{1'}$—COCl, thereby to introduce $R^1$ therein to obtain a compound 10 of the present invention (the following formula (17)), followed by deprotection in the same manner (FIG. 3).

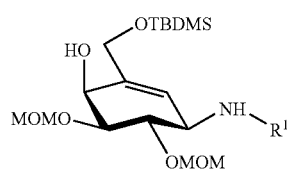

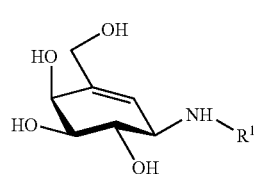

Also, it is possible to obtain a compound 13 of the present invention (a dialkyl compound: the following formula (19), wherein $R^1$ and $R^2$ are both alkyl groups in the formulae (19), (20), (21) and (22)), by re-binding $R^2$ (wherein the $R^2$ herein is the same as the alkyl group of formula (1)) to the compound 10 of the present invention, followed by deprotection. In addition, a compound 16 of the present invention (the following formula (22)) can also be obtained by acylating the compound 10 of the present invention in the same manner (compound 14: the following formula (20)), followed by reduction by lithium aluminum hydride (compound 15: the following formula (21)) and subsequent deprotection.

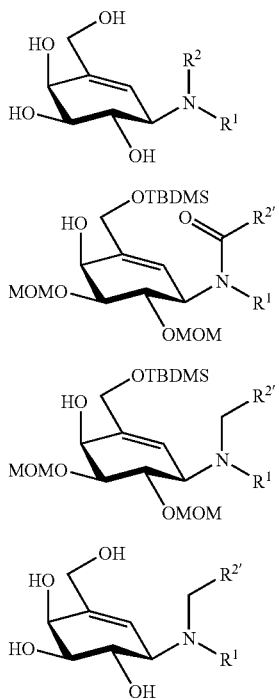

(19)

(20)

(21)

(22)

(2) Drug 1 of the Present Invention

The drug 1 of the present invention is a glycolipid metabolic disorder treating agent comprising the aforementioned substance of the present invention as an active ingredient.

Since the substance of the present invention shows a specific and strong inhibitory activity against human normal β-galactosidase and also has an activity to regenerate, in the living body, the activity of the human β-galactosidase whose enzyme activity was reduced or lost due to a mutation, it becomes an excellent agent for treating glycolipid metabolic disorders caused by the mutation of β-galactosidase gene.

The term "agent for treating glycolipid metabolic disorders" as used herein is an idea including a "therapeutic agent" for curing or alleviating symptoms after onset of a glycolipid metabolic disorder (e.g., $GM_1$ gangliosidosis, Morquio-B disease, Krabbe's disease or the like) induced by a mutation of β-galactosidase, and a "preventive agent" for preventing onset of the disease.

Any one of the compounds represented by the following formula (1) can be used as the substance of the present invention which is the active ingredient of the drug 1 of the present invention.

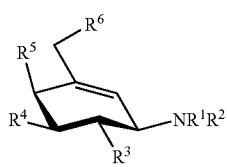

(1)

In this case, each of $R^1$ and $R^2$ independently represents H, an alkyl group, an alkenyl group, an alkynyl group, an acyl group, an aryl group or an aralkyl group, wherein both are not H at the same time, and each of $R^3$, $R^4$, $R^5$ and $R^6$ independently represents a hydroxyl group or a hydroxyl group having a substituent.

Among these, it is desirable that one of $R^1$ and $R^2$ is H and the other is an alkyl group, and all of $R^3$, $R^4$, $R^5$ and $R^6$ are hydroxyl groups. The aforementioned alkyl group is preferably a straight or branched chain alkyl group having from 1 to 23 carbon atoms, particularly preferably a straight chain alkyl group. It is particularly desirable that the number of carbon atoms is from 2 to 20. In addition, examples of the most desirable substance as the active ingredient include the substance 18 of the present invention. This is because these desirable substances of the present invention have particularly significant effects in accelerating stabilization of the mutated enzyme and regenerating its activity.

In this connection, the β-galactosidase inhibitory activity possessed by the carba-sugar amine derivative as the active ingredient of the drug 1 of the present invention can be calculated by adding a substance to be tested to a solution containing β-galactosidase and its substrate and comparing the enzyme activity with that in the case where the substance of the present invention is not added.

The aforementioned drug 1 of the present invention can be made into dosage forms such as tablets, capsules, solutions, injections, granules, powders, emulsions, and inhalation powders according to the administration route such as oral administration or injection, objects, subjects and the like. Although it is not particularly limited, it is desirable that the active ingredient in the drug 1 of the present invention is set to a concentration of from 0.001 to 5%. For example, it is preferably 0.01% (W/V) or more, more preferably from 0.03% to 0.2% (W/V), when the drug 1 of the present invention is made into solutions for oral administration. Also, it is preferably 0.01% (W/V) or more, most preferably from 0.03% (W/V) or more, when used as injections for intramuscular injection or intravenous injection.

(3) Drug 2 of the Present Invention

The drug 2 of the present invention is a glycolipid metabolic disorder treating agent containing a carba-sugar amine derivative represented by the following formula (2) as the active ingredient.

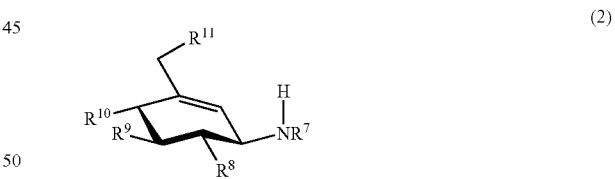

(2)

In this case, $R^7$ represents an alkyl group, and each of $R^8$, $R^9$, $R^{10}$ and $R^{11}$ independently represents a hydroxyl group or a hydroxyl group having a substituent.

$R^7$ is an alkyl group, and examples of the alkyl group include straight or branched chain alkyl groups having from 1 to 23, and particularly straight chain alkyl groups having from 2 to 20 carbon atoms is desirable. Specifically, since the drug 2 of the present invention is applied to diseases induced by abnormality of sphingoglycolipid metabolic system, it is desirable that the active ingredient thereof is an analog of a sphingoglycolipid. That is, it is most desirable that the alkyl group of $R^7$ in the formula (2) is an alkyl group having from 2 to 18 carbon atoms, which becomes an analog of a sphingoglycolipid having from 2 to 18 carbon atoms mainly existing in the living body.

Each of $R^8$, $R^9$, $R^{10}$ and $R^{11}$ independently represents a hydroxyl group or a hydroxyl group having a substituent, and a hydroxyl group is particularly desirable. In this case, although it is not particularly limited, examples of the substituent groups of $R^8$, $R^9$, $R^{10}$ and $R^{11}$ include, aralkyl groups (benzyl group, phenethyl group, α-methylbenzyl group and the like), silyl groups (trimethylsilyl group, triethylsilyl group, triisopropylsilyl (TIPS) group, t-butyldiphenylsilyl (TBDPS) group, t-butyldimethylsilyl (TBDMS) group and the like), alkanoyl groups (acetyl group, butyryl group and the like), aroyl groups (benzoyl group, toluoyl group, naphthoyl group and the like), alkoxy alkyl groups (methoxymethyl (MOM) group and the like) and aralkyloxy alkyl groups (benzyloxymethyl (BOM) group and the like). Among these, MOM group is particularly desirable from the viewpoint of its stability and easy handling and elimination.

In this connection, since the carba-sugar amine derivative as the active ingredient of the drug 2 of the present invention is a kind of pseudo-sugar, provision of carbon numbers is described herein by the method shown in the following structural formula (23) in accordance with the case of hexose.

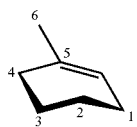
(23)

Also, with regard to the alkylamino group represented by $NHR^7$ in the formula (2), when it is supposed that the pseudo-sugar, carba-sugar amine, is a hexose (when the carbon bonded to the 1-position and 5-position carbons in the aforementioned formula (23) is supposed to be the oxygen of the six-membered ring of hexose), and when the alkylamino group ($NHR^7$) bonded to the 1-position is positioned on the upper side of the six-membered ring, it is called β type, or α type when it is on the opposite side, then the carba-sugar amine derivative as the active ingredient of the drug 2 of the present invention is β type.

With regard to the carba-sugar amine derivative as the active ingredient of the drug 2 of the present invention, a substance represented by the following formula (24) in which $R^7$ is a straight chain alkyl group is the most preferable active ingredient of the drug 2 of the present invention:

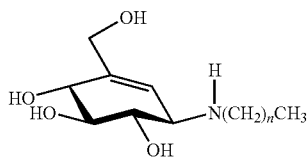
(24)

wherein n=0-22.

Since such a substance shows a stabilizing activity upon β-glucocerebrosidase derived from a mammal, particularly human, it can be used as a β-glucocerebrosidase stabilizing agent or as a glycolipid metabolic disorder treating agent containing it as the active ingredient.

In this connection, the term "glycolipid metabolic disorder treating agent" as used herein is an idea including a "therapeutic agent" for curing or alleviating symptoms after onset of a glycolipid metabolic disorder (Gaucher's disease or the like) induced by a mutation of β-glucocerebrosidase, and a "preventive agent" for preventing onset of the disease.

This substance can be prepared by the method described in *Bioorganic and Medicinal Chemistry Letters*, 6(8), 929-932 (1996).

Since the carba-sugar amine derivative represented by the formula (2) shows a specific and strong inhibitory activity against human β-glucosidase and also has a function to regenerate, in the living body, the activity of the human β-glucosidase whose enzyme activity was reduced or lost, it can become an effective agent for treating glycolipid metabolic disorders caused by the mutation of β-glucosidase gene.

In this connection, the β-glucosidase inhibitory activity possessed by the carba-sugar amine derivative as the active ingredient of the drug 2 of the present invention can be calculated by adding a substance to be tested to a solution containing β-glucosidase and its substrate and comparing the enzyme activity with that in the case where the substance of the present invention is not added.

The aforementioned drug 2 of the present invention can be made into dosage forms such as tablets, capsules, solutions, injections, granules, powders, emulsions, and inhalation powders according to administration route such as the oral administration or injection, objects, subjects. Although it is not particularly limited, it is desirable that the active ingredient in the drug 2 of the present invention is set to a concentration of from 0.001 to 5%. For example, it is preferably 0.01% (W/V) or more, more preferably from 0.03% to 0.2% (W/V), when the drug 2 of the present invention is made into solutions for oral administration. Also, it is preferably 0.01% (W/V) or more, more preferably from 0.03% (W/V) or more, when used as injections for intramuscular injection or intravenous injection.

84GG, closed diamond shows a fibroblast of a genotype L444P/PecNci, and open square shows a fibroblast of a genotype L444P/L444P.

Figure 11:
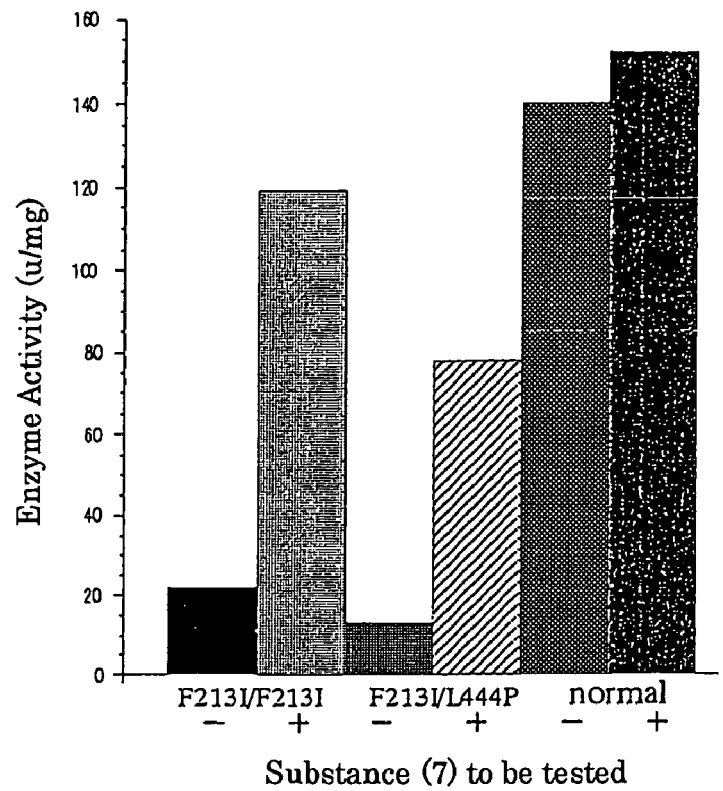

FIG. 11 is a graph showing changes in the β-glucocerebrosidase activity in fibroblast cultures in the presence of 30 μmol/liter of a carba-sugar amine derivative.

Figure 12:
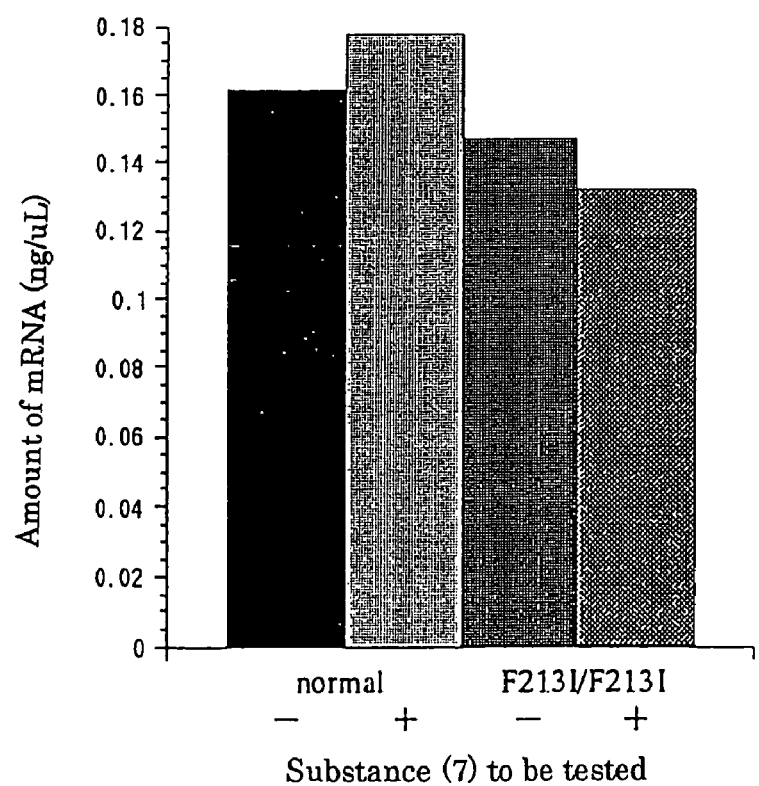

FIG. 12 is a graph showing changes in the transcription of β-glucocerebrosidase gene in fibroblast cultures in the presence of a carba-sugar amine derivative.

Figure 13:
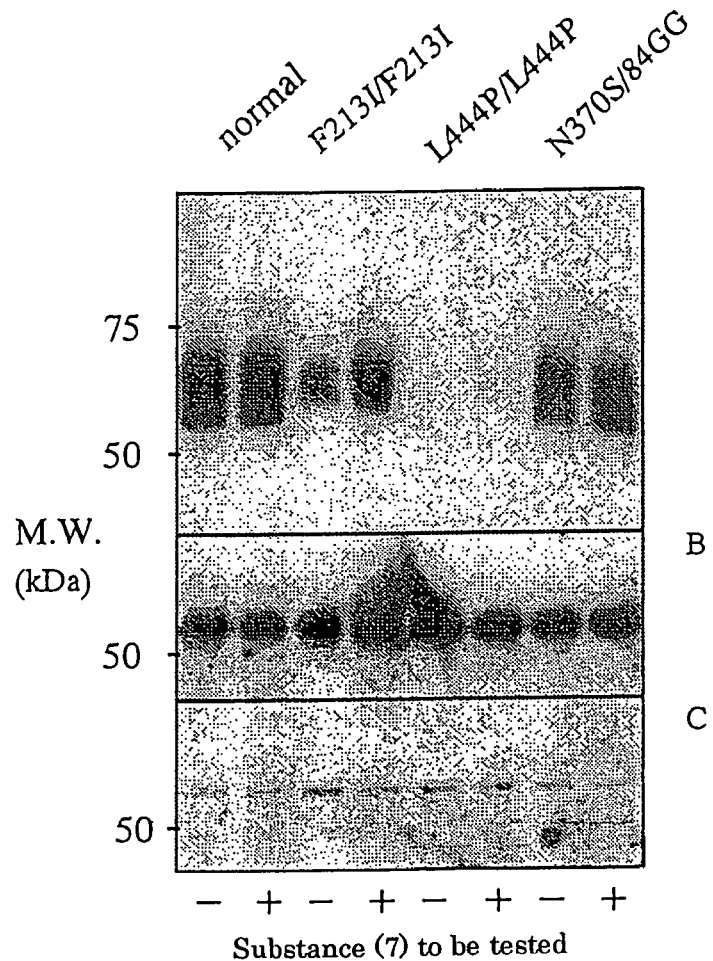

FIG. 13 is a photograph showing changes in the amount of β-glucocerebrosidase enzyme by a carba-sugar amine derivative in cultured fibroblast. A shows the enzyme protein band of β-glucocerebrosidase, B shows that of hexosaminidase A, and C shows that of hexosaminidase B.

Figure 14:
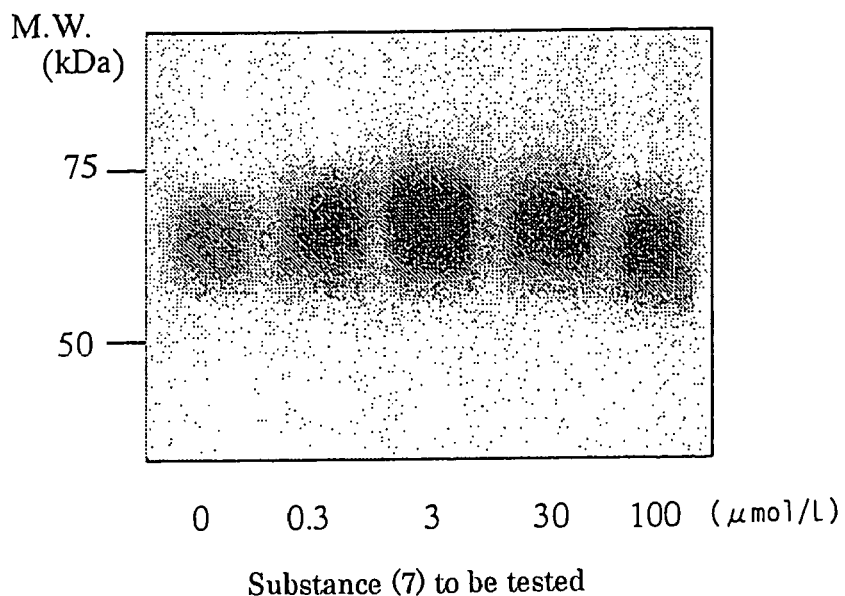

FIG. 14 is a photograph showing influence of the concentration of a carba-sugar amine derivative upon changes in the amount of β-glucocerebrosidase enzyme.

Figure 15:
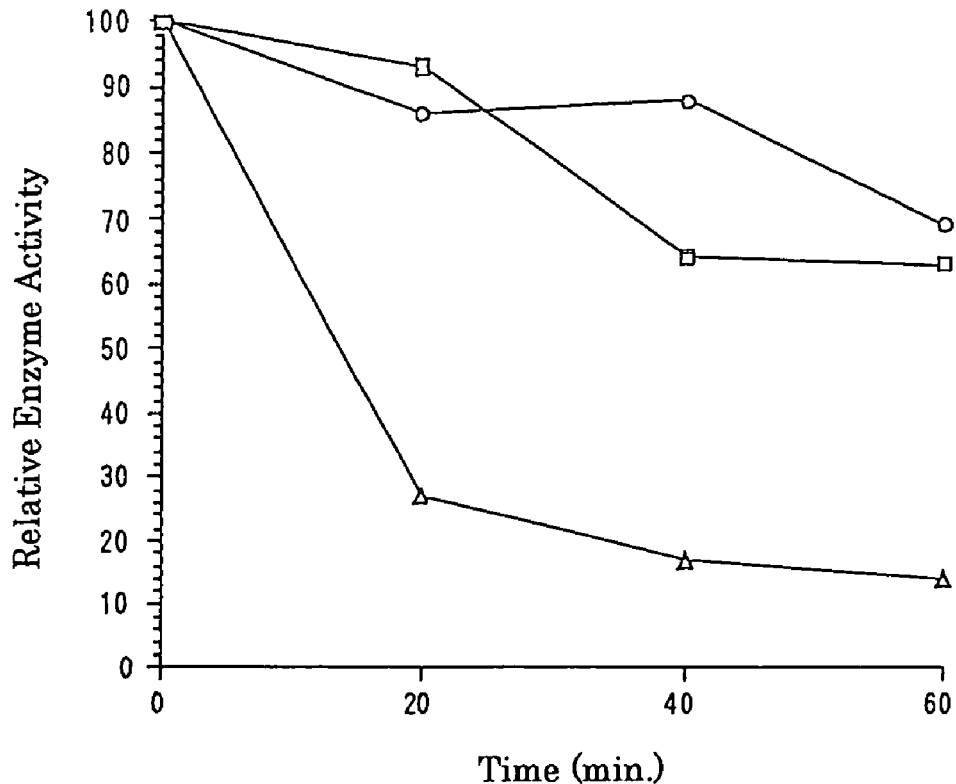

FIG. 15 is a graph showing pH-stability of β-glucocerebrosidase in a supernatant of fibroblast derived from a patient of Gaucher's disease. Closed circle indicates pH 5, closed square indicates pH 6, and closed triangle indicates pH 7.

Figure 16:
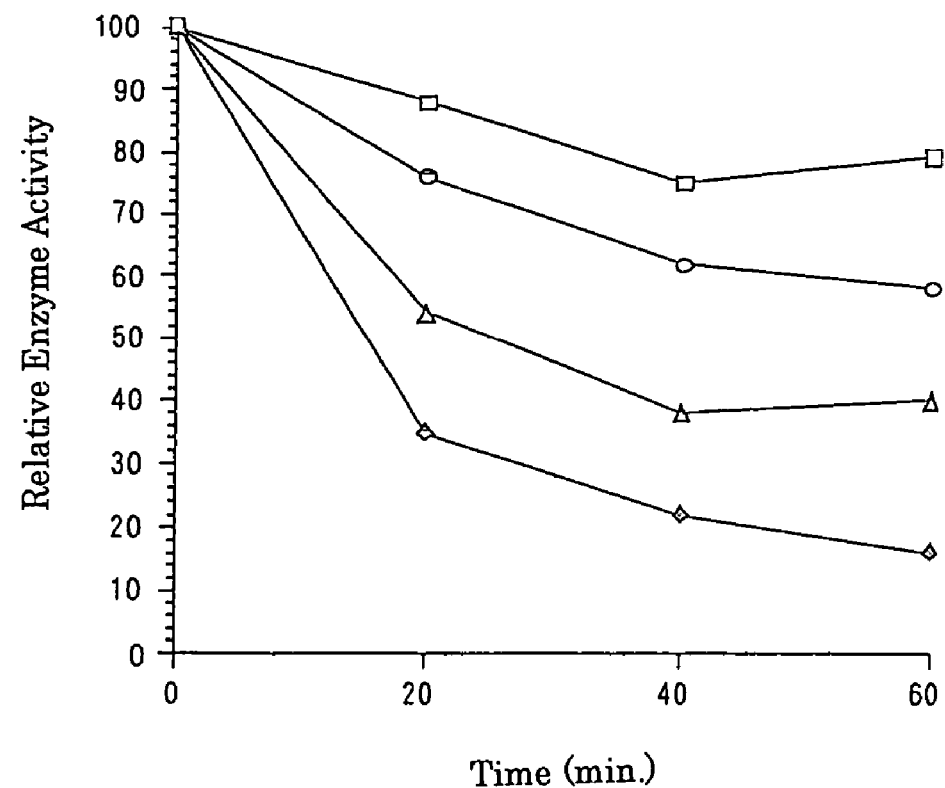

FIG. 16 is a graph showing stabilizing effect of a carba-sugar amine derivative at pH 7 upon β-glucocerebrosidase in a supernatant of fibroblast derived from a patient of Gaucher's disease. Closed diamond is a case when a substance (7) to be tested was not added, closed triangle is a case in which 0.1 μmol/liter of the substance (7) to be tested was added, closed circle is a case in which 1 μmol/liter of the substance (7) to be tested was added, and closed square is a case in which 10 μmol/liter of the substance (7) to be tested was added.

Figure 17:
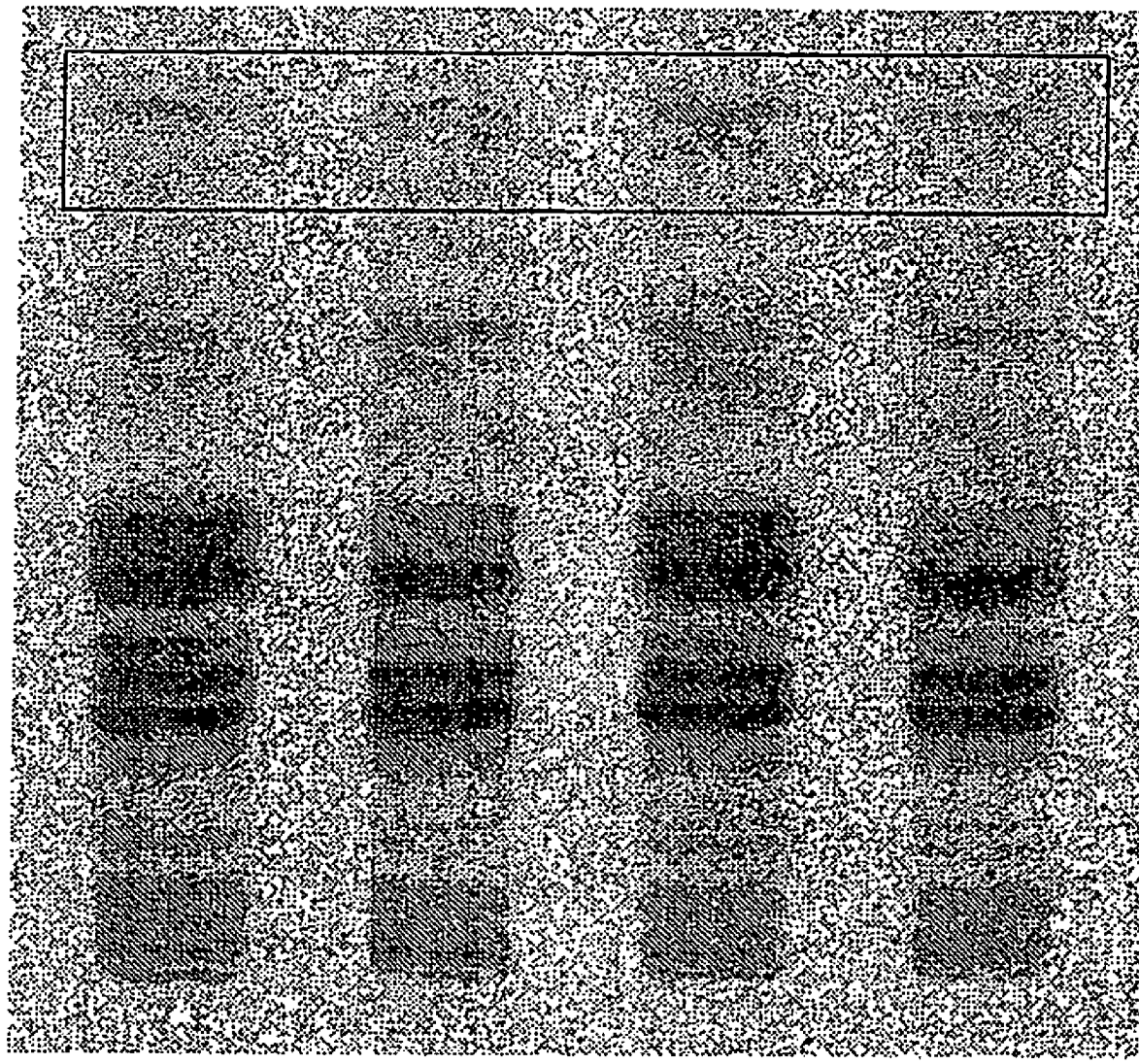

FIG. 17 is a photograph of a result of an autoradiography showing effect of a carba-sugar amine derivative upon changes in the amount of glucocerebroside by β-glucocerebrosidase activity.

Figure 18:
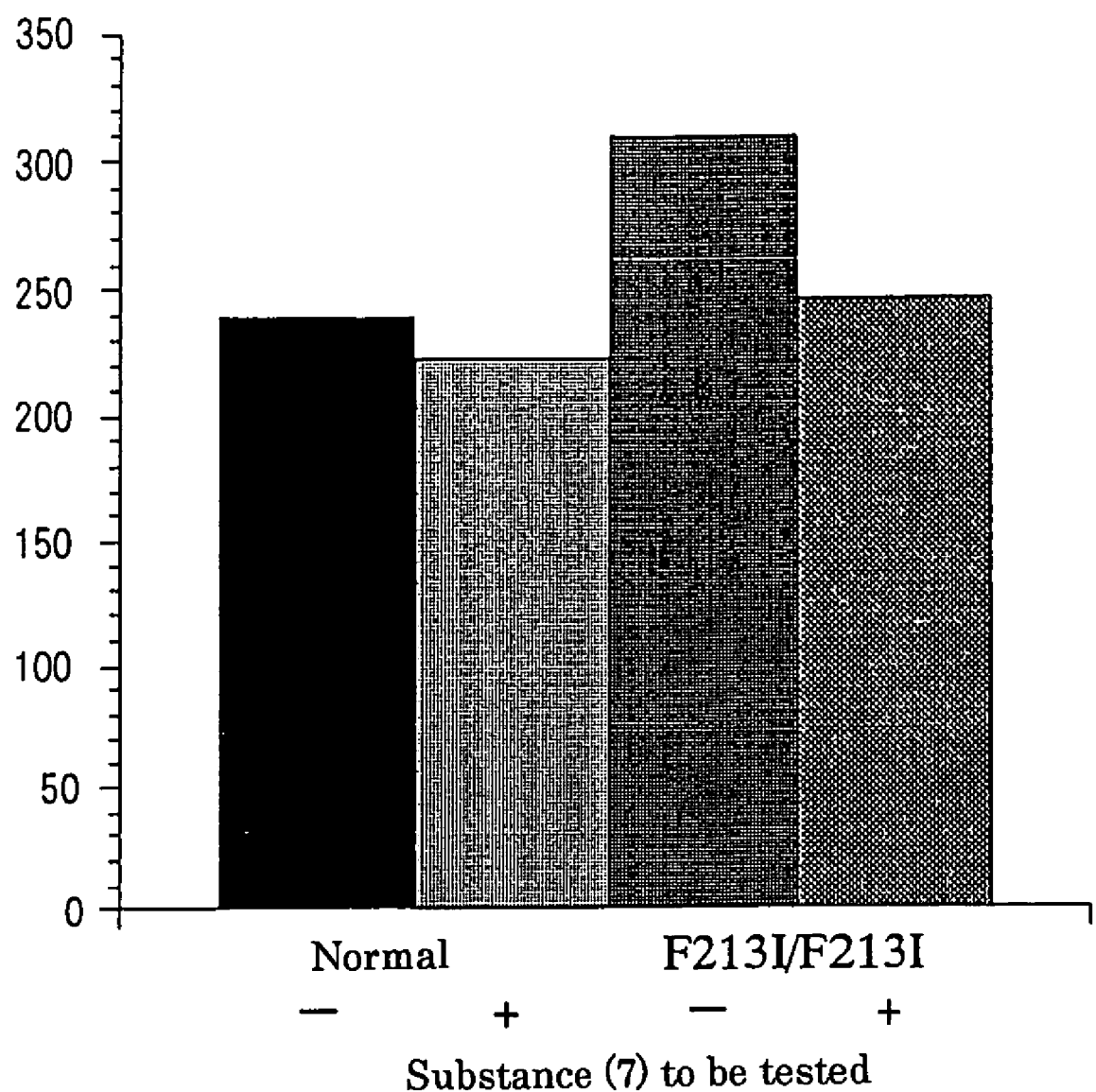

FIG. 18 is a graph showing determination of images by an autoradiography.

BEST MODE FOR CARRYING OUT THE INVENTION

The present invention is described below in detail based on examples.

<1> Synthesis of the Substance of the Present Invention (N-octyl Substitution Product: n=7 in the Aforementioned Formula (4))

(1) Synthesis of N-octyl-N-tert-butoxycarbonyl-1-deoxy-2,3:4,6-di-O-isopropylidene-5a-carba-β-D-xylo-hexo-5(5a)-enopyranosylamine (compound 12)

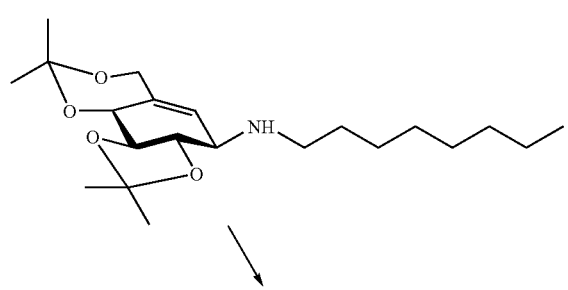

-continued

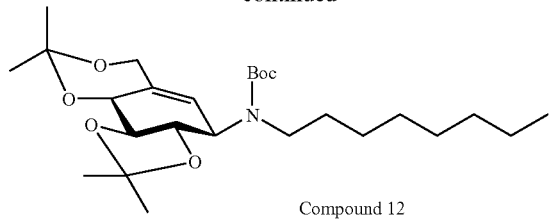

Compound 12

In the formula, Boc represents a tert-butoxycarbonyl group. The same shall apply hereinafter.

Triethylamine (0.97 ml, 7.01 mmol) and di-tert-butyl dicarbonate (0.81 ml, 3.50 mmol) were added to a dichloromethane solution (13 ml) of N-octyl-2,3:4,6-di-O-isopropylidene-5a-carba-β-D-xylo-hexo-5(5a)-enopyranosylamine (644 mg, 1.75 mmol) prepared by the method described in *Bioorganic & Medicinal Chemistry Letters*, 6 (1996), 929-932, and the mixture was stirred at room temperature for 1.5 hours. Triethylamine (0.97 ml, 7.01 mmol) and tert-butyl dicarbonate (0.81 ml, 3.50 mmol) were added thereto, followed by stirring for further 1 hour. After diluting the reaction mixture with 180 ml of ethyl acetate, the solution was washed twice with 60 ml of an aqueous sodium bicarbonate solution and 60 ml of brine and then dried and concentrated.

The crude product was purified by silica gel chromatography (50 g, density gradient elution method, 1:11→1:8 ethyl acetate/hexane) to obtain the compound 12 as a colorless oily substance (807 mg, yield 99%).

TLC: Rf=0.49 (1:5 ethyl acetate/toluene)

$[\alpha]^{22}_D$: −61° (c=0.90 chloroform)

IR (Neat): υ(cm$^{-1}$)=2960 (CH$_3$), 2930 or 2855 (CH$_2$), 1695 (amide)

$^1$H NMR (300 MHz, (CD$_3$)$_2$SO, 110° C.)

δ=5.22 (br s, 1H, H-5a), 4.59 (br d, 1H, J$_{4,3}$=9.3 Hz, 4-H), 4.57 (br d, 1H, J$_{1,2}$=9.3 Hz, 1-H), 4.40 and 4.13 (2d, each 1H, J$_{gem}$=13.7 Hz, 6,6-H), 3.74 (dd, 1H, J$_{2,3}$=9.3 Hz, 2-H), 3.59 (dd, 1H, 3-H), 3.11 and 2.93 (2m, each 1H, NCH$_2$), 1.54-1.18 (m, 12H, 6×CH$_2$), 1.47, 1.37, 1.36 and 1.29 (4s, each 3H, 2×CMe$_2$), 1.40 (s, 9H, t-Bu), 0.86 (t, 3H, J=6.6 Hz, CH$_2$CH$_3$)

Elementary Analysis

Calculated Value C$_{26}$H$_{45}$NO$_6$: C, 66.78; H, 9.70; N, 3.00.

Actual Value: C66.57; H, 10.10; N, 3.11.

(2) Synthesis of N-octyl-N-tert-butoxycarbonyl-1-deoxy-5a-carba-β-D-xylo-hexo-5(5a)-enopyranosylamine (compound 13)

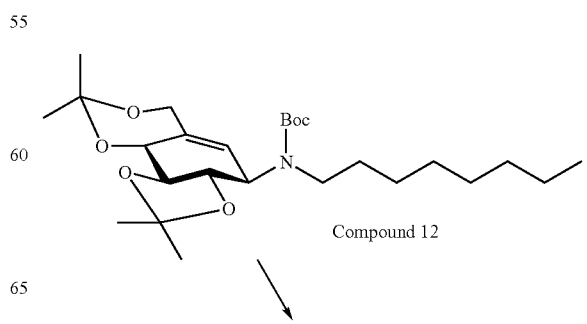

Compound 12

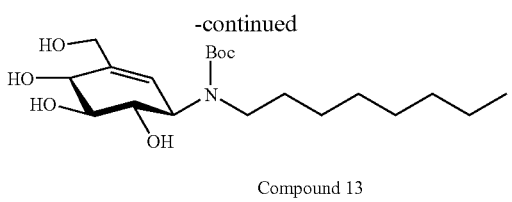

Compound 13

The compound 12 (768 mg, 1.64 mmol) and 60% acetic acid solution (16 ml) were stirred at 60° C. for 30 minutes and then concentrated. The residue was evaporated three times with ethanol. The crude product was purified by a column chromatography (density gradient elution method, 1:10→1:4 ethanol/toluene) using silica gel (47 g) to obtain the compound 13 as a colorless oily substance (539 mg, yield 85%).

TLC: Rf=0.54 (1:5 methanol/chloroform)

$[\alpha]^{20}_D$: −87° (c=1.10 methanol)

IR (KBr-Disk): $\upsilon(cm^{-1})$=3445 (OH), 2960 ($CH_3$), 2930 or 2855 ($CH_2$)

$^1$H NMR (270 MHz, 1:2 $CD_3OD/CDCl_3$)

δ=5.42 (br s, 1H, H-5a), 4.38-4.05 (m, 2H, H-1, H-4), 4.20 and 4.10 (2d, each 1H, $J_{gem}$=13.4 Hz, 6,6-H), 3.72 (dd, 1H, $J_{1,2}$=9.2 Hz, $J_{2,3}$=9.5 Hz, 2-H), 3.31 (dd, 1H, $J_{2,3}$=9.5 Hz, $J_{3,4}$=8.0 Hz, 3-H), 3.26 (m, 1H, 1'a-H), 3.01 (m, 1H, 1'b-H), 1.73-1.18 (m, 12H, $CH_2$×6: H-2'-H-7'), 1.47 (s, 9H, t-Bu: Boc), 0.89 (t, 3H, J=6.4 Hz, $CH_2CH_3$)

(3) Synthesis of N-octyl-N-tert-butoxycarbonyl-4,6-O-benzylidene-5a-carba-β-D-xylo-hexo-5(5a)-enopyranosylamine (compound 14)

for further 2 hours. The reaction mixture was diluted with 60 ml of ethyl acetate, and the solution was washed with 20 ml of water, 20 ml of a saturated aqueous sodium bicarbonate solution and 20 ml of water in that order, dried with sodium sulfate, filtered and then concentrated. When this concentrate was analyzed by thin layer chromatography, two components were detected (Rf 0.33 and 0.74: acetone/toluene, 1:5, Rf 0.05 and 0.70: ethyl acetate/toluene, 1:5).

The crude product was subjected to silica gel chromatography (16 g, density gradient elution method, 1:24->1:3 ethyl acetate/toluene) to obtain a 2,3:4,6-di-O-benzylidene-added compound as a colorless oily substance (compound 15: first elution fraction: 159 mg, yield 45%) and the compound 14 as a colorless oily substance (compound 17: 164 mg, yield 55%).

After dissolving the compound 15 in 5 ml of methanol, p-toluenesulfonic acid monohydrate (3 mg, 0.016 mmol) was added thereto at 0° C., followed by stirring for 10 minutes, and then the mixture was neutralized by adding dropwise triethylamine and concentrated. The crude product was purified by silica gel chromatography (7 g, 1:7 acetone/toluene) to obtain the compound 14 (110 mg, 82% as combined yield with the direct reaction product from the compound 16).

TLC: Rf=0.33 (1:5 acetone/toluene)

$[\alpha]^{22}_D$: −57° (c=0.97 chloroform)

IR (neat): $\upsilon(cm^{-1})$=3420 (OH), 2960 ($CH_3$), 2925 or 2855 ($CH_2$), 1695 (amide)

$^1$H NMR (300 MHz, $(CD_3)_2SO$, 110° C.)

δ=7.46-7.27 (m, 5H, Ph), 5.65 (s, 1H, CHPh), 5.31 (br s, 1H, 5a-H), 4.39 (br s, 2H, 6, 6-H), 4.36 (br d, 1H, $J_{3,4}$=7.6 Hz, 4-H), 4.16 (br s, 1H, 1-H), 3.64 (dd, 1H, $J_{1,2}$=$J_{2,3}$=9.3 Hz, 2-H), 3.52 (dd, 1H, 3-H), 3.25-2.80 (m, 2H, $NCH_2$), 1.57-1.17 (m, 12H, 6×$CH_2$), 1.39 (s, 9H, $CMe_3$), 0.87 (t, 3H, J=6.2 Hz, $CH_2CH_3$).

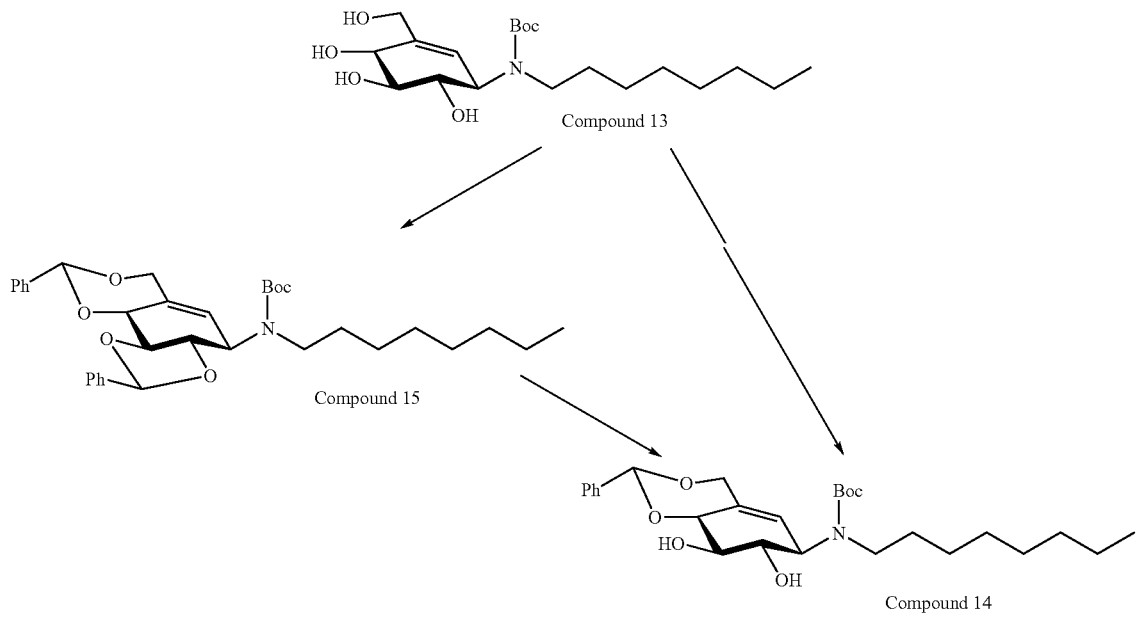

α,α-Dimethoxytoluene (112 µl, 0.746 mmol) and p-toluenesulfonic acid monohydrate (12 mg, 0.063 mmol) were added to a DMF solution (6 ml) of the compound 13 (242 mg, 0.624 mmol), followed by stirring at 45° C. for 3.5 hours under a reduced pressure. α,α-Dimethoxytoluene (50 µl, 0.333 mmol) was further added thereto, followed by stirring Elementary Analysis Calculated Value $C_{27}H_{41}NO_6$·$0.5H_2O$: C, 66.92; H, 8.73; N, 2.89.

Actual Value: C, 66.94; H, 8.85; N, 2.91.

(4) Synthesis of N-octyl-N-tert-butoxycarbonyl-4,6-O-benzylidene-2,3-di-O-methoxymethyl-5a-carba-β-D-xylo-hexo-5(5a)-enopyranosylamine (compound 16)

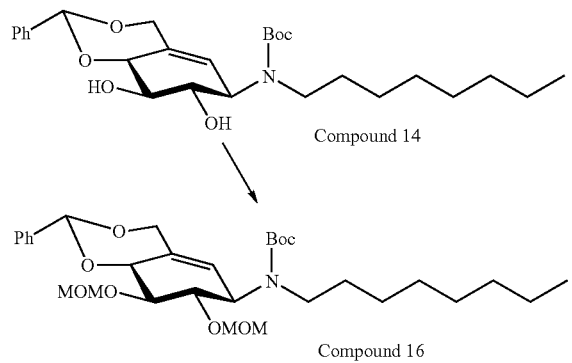

Chloromethyl ether (0.43 ml, 5.66 mmol) and N,N-diisopropylethylamine (1.97 ml, 11.31 mmol) were added to a 1,2-dichloroethane solution (7 ml) of the compound 14 (269 mg, 0.566 mmol), followed by stirring at 60° C. for 3 hours. The reaction mixture was diluted with 60 ml of chloroform, washed with 30 ml of 1 mol/liter hydrochloric acid, 30 ml of a saturated aqueous sodium bicarbonate solution and 30 ml of water in this order and then concentrated. The crude product was subjected to silica gel chromatography (20 g, density gradient elution, 1:14→1:9 ethyl acetate/toluene) to obtain the compound 16 as a colorless oily substance (315 mg, yield 99%).

TLC: Rf=0.44 (1:5 ethyl acetate/toluene)

$[\alpha]^{21}_D$: −126° (c=1.10 chloroform)

IR (neat): $\upsilon(cm^{-1})$=2960 ($CH_3$), 2925 or 2855 ($CH_2$), 1695 (amide)

$^1H$ NMR (300 MHz, $(CD_3)_2SO$, 110° C.)

δ=7.45-7.28 (m, 5H, Ph), 5.70 (s, 1H, CHPh), 5.38 (br s, 1H, 5a-H), 4.79 and 4.77 (2d, each 1H, $J_{gem}$=6.1 Hz) and 4.75 and 4.63 (2d, each 1H, $J_{gem}$=6.3 Hz) (2×$OCH_2$), 4.57 (br d, 1H, $J_{3,4}$=7.7 Hz, 4-H), 4.43 (br s, 2H, 6,6-H), 4.27 (br s, 1H, 1-H), 3.99 (dd, 1H, $J_{1,2}$=9.3 Hz, $J_{2,3}$=10.0 Hz, 2-H), 3.78 (dd, 1H, 3-H), 3.28-3.27 (2s, each 3H, 2×OMe), 3.07-2.87 (m, 2H, $NCH_2$), 1.62-1.20 (m, 12H, 6×$CH_2$), 1.39 (s, 9H, t-Bu), 0.87 (t, 3H, J=6.5 Hz, $CH_2CH_3$)

Elementary Analysis

Calculated Value $C_{31}H_{49}NO_8$: C, 66.05; H, 8.76; N, 2.48.

Actual Value: C, 65.80; H, 8.99; N, 2.42.

(5) Synthesis of N-octyl-N-tert-butoxycarbonyl-2,3-di-O-methoxymethyl-5a-carba-β-D-xylo-hexo-5(5a)-enopyranosylamine (compound 17)

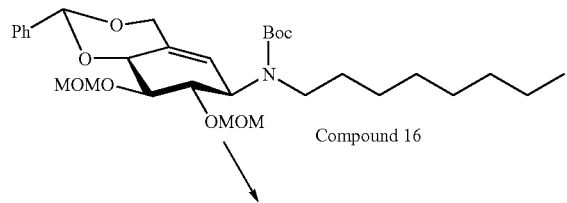

-continued

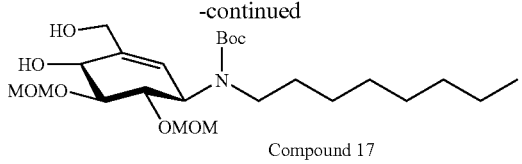

A 60% acetic acid solution (8 ml) of the compound 16 (315 mg, 0.559 mmol) was stirred at 60° C. for 2 hours and then concentrated. The residue was evaporated three times using ethanol and then evaporated three times using toluene. The crude product of compound 17 was subjected to silica gel chromatography (20 g, density gradient elution, 1:6→1:5 acetone/toluene) to obtain the compound 17 as a colorless oily substance (216 mg, yield 83%).

TLC: Rf=0.13 (1:5 acetone/toluene)

$[\alpha]^{20}_D$: −141° (c=1.11 chloroform)

IR (neat): $\upsilon(cm^{-1})$=3440 (OH), 2955 ($CH_3$), 2925 or 2855 ($CH_2$), 1695 (amide)

$^1H$ NMR (300 MHz, $(CD_3)_2SO$, 110° C.)

δ=5.32 (br s, 1H, H-5a), 4.83 and 4.76 (2d, each 1H, $J_{gem}$=5.6 Hz, $CH_2$: MOM), 4.73 and 4.61 (2d, each 1H, $J_{gem}$=5.9 Hz, $CH_2$: MOM), 4.23 (br s, 1H, 1-H), 4.10 (br s, 1H, 4-H), 3.99 (br s, 2H, 6,6-H), 3.84 (dd, 1H, $J_{1,2}$=8.8 Hz, $J_{2,3}$=9.5 Hz, 2-H), 3.52 (dd, 1H, $J_{2,3}$=9.5 Hz, $J_{3,4}$=7.8 Hz, 3-H), 3.36 and 3.26 (2s, each 3H, 2×$CH_3$: MOM), 3.26-2.83 (m, 2H, H-1'a, 1'b-H), 1.63-1.17 (m, 12H, $CH_2$×6: H-2'-H-7'), 1.38 (s, 9H, t-Bu: BOC), 0.86 (t, 3H, J=6.1 Hz, $CH_2CH_3$)

(6) Synthesis of N-octyl-N-tert-butoxycarbonyl-2,3-di-O-methoxymethyl-6-O-tert-butyldimethylsilyl-5a-carba-β-D-xylo-hexo-5(5a)-enopyranosylamine (compound 18)

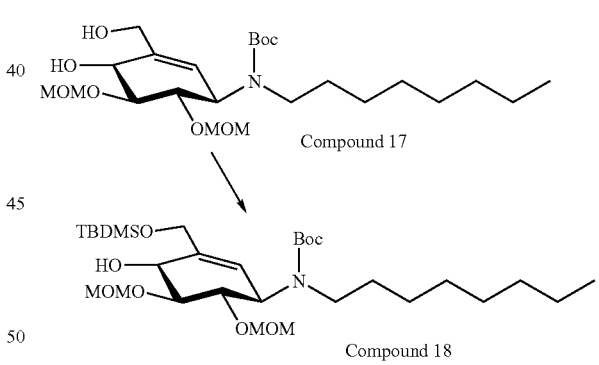

Imidazole (91 mg, 1.34 mmol) and tert-butylchlorodimethylsilane (100 mg, 0.670 mmol) were added to an N,N'-dimethylformamide (to be referred to as "DMF" hereinafter) solution (5 ml) of the compound 17 (159 mg, 0.334 mmol), followed by stirring at room temperature for 1 hour. The reaction mixture was diluted with 60 ml of ethyl acetate, washed three times with 20 ml of water, dried with sodium sulfate, filtered and then concentrated. The crude product of compound 18 was subjected to silica gel chromatography (20 g, 1:6 ethyl acetate/toluene) to obtain the compound 18 as a colorless oily substance (194 mg, yield 98%).

TLC: Rf=0.24 (1:5 ethyl acetate/toluene)

$[\alpha]^{23}_D$: −101° (c=0.95 chloroform)

IR (neat): $\upsilon(cm^{-1})$=3445 (OH), 2955 ($CH_3$), 2925 or 2855 ($CH_2$), 1695 (amide)

$^1$H NMR (300 MHz, (CD$_3$)$_2$SO, 110° C.)

δ=5.36 (br s, 1H, 5a-H), 4.83 and 4.76 (2d, each 1H, J$_{gem}$=6.1 Hz) and 4.73 and 4.60 (2d, each 1H, J$_{gem}$=6.3 Hz) (2×OCH$_2$), 4.21 and 4.11 (ABq, J$_{gem}$=13.9 Hz, 6,6-H), 4.12-4.04 (m, 2H, 1-H, 4-H), 3.87 (dd, 1H, J$_{1,2}$=9.3 Hz, J$_{2,3}$=9.9 Hz, 2-H), 3.53 (dd, 1H, J$_{3,4}$=7.9 Hz, 3-H), 3.35 and 3.26 (2s, each 3H, 2×OCH$_3$), 3.05-2.88 (m, 2H, NCH$_2$), 1.60-1.20 (m, 12H, 6×CH$_2$), 1.38 (s, 9H, OCMe$_3$), 0.89 (s, 9H, CCMe$_3$), 0.86 (t, 3H, J=6.8 Hz, CH$_2$CH$_3$), 0.05 (s, 6H, SiMe$_2$).

Elementary Analysis

Calculated Value C$_{30}$H$_{59}$NO$_8$Si: C, 61.08; H, 10.08; N, 2.37.

Actual Value: C, 60.82; H, 10.38; N, 2.45.

(7) Synthesis of N-octyl-N-tert-butoxycarbonyl-2,3-di-O-methoxymethyl-6-O-tert-butyldimethylsilyl-5a-carba-α-L-arabino-hexo-5(5a)-enopyranosylamine (substance 17 of the present invention)

Powdery 4 Å molecular sieve (75 mg) and pyridinium chlorochromate (41 mg, 0.190 mmol) were added to a dichloromethane solution (2 ml) of the compound 18 (75 mg, 0.127 mmol), followed by stirring at room temperature for 1 hour. Pyridinium chlorochromate (41 mg, 0.190 mmol) was further added thereto followed by stirring for further 1 hour. The mixture was passed through a celite filter and then applied to a short silica gel column (eluent: diethyl ether). The eluate was evaporated to obtain a crude ketone, and then the ketone compound was dissolved in tetrahydrofuran (to be referred to as "THF" hereinafter) (0.7 ml) and treated with 1 mol/L (hereinafter, mol/L is also represented by M) lithium-tri-sec-butyl borohydride/THF solution (0.51 ml, 0.51 mmol) at −78° C. for 30 minutes under an atmosphere of argon. The reaction mixture was warmed up to 0° C., and the reaction was stopped with saturated ammonium chloride. This reaction mixture was mixed with magnesium sulfate and then subjected to celite filtration. The eluate was evaporated and subjected to silica gel chromatography (7 g, density gradient elution, 1:9→1:6 ethyl acetate/toluene) to obtain the substance 17 of the present invention as a colorless oily substance (49.1 mg, yield 66%).

TLC: Rf=0.16 (1:5 ethyl acetate/toluene)

[α]$^{23}$$_D$: −68° (c=1.125 chloroform)

IR (neat): υ(cm$^{-1}$)=3460 (OH), 2955 (CH$_3$), 2930 or 2855 (CH$_2$), 1695 (amide)

$^1$H NMR (300 MHz, (CD$_3$)$_2$SO, 110° C.)

δ=5.36 (br s, 1H, 5a-H), 4.71 and 4.59 (2d, each 1H, J$_{gem}$=5.6 Hz,) and 4.75-4.66 (m, 2H) (2×OCH$_2$), 4.38 (br s, 1H, 1-H), 4.19 and 4.12 (2d, each 1H, J$_{gem}$=13.2 Hz, 6,6-H), 4.13-4.02 (m, 2H, 2-H, 4-H), 3.46 (dd, 1H, J$_{2,3}$=10.3 Hz, J$_{3,4}$=2.0 Hz, 3-H), 3.33 and 3.25 (2s, each 3H, 2×OM$_2$), 3.10-2.86 (m, 2H, 1',1'-H), 1.62-1.16 (m, 12H, 6×CH$_2$), 1.39 (s, 9H, CCMe$_3$), 0.89 (s, 9H, SiCMe$_3$), 0.86 (t, 3H, J=7.3 Hz, CH$_2$CH$_3$), 0.05 (s, 6H, SiMe$_2$).

Elementary Analysis

Calculated Value C$_{30}$H$_{59}$NO$_8$Si: C, 61.08; H, 10.08; N, 2.37.

Actual value: C, 60.80; H, 10.37; N, 2.53.

(8) Synthesis of N-octyl-5a-carba-α-L-arabino-hexo-5(5a)-enopyranosylamine (substance 18 of the present invention of formula (1) (R$^1$=octyl group, R$^2$, R$^3$, R$^4$, R$^5$ hydroxyl group)

To the substance 17 of the present invention (29 mg, 0.049 mmol) dissolved in THF (0.5 ml), 4 μmol/liter of hydrochloric acid (1.5 ml) was added, followed by stirring at 65° C. for 1.5 hours and then concentrated. The residue was evaporated three times using ethanol. The thus formed product was purified using an ion exchange column (Dowex 50-X2 (H$^+$)). Using 1% methanol ammonium for the elution, the compound 18 of the present invention was obtained as a white solid (12.8 mg, yield 91%).

Melting point: 126~128° C.

TLC: Rf=0.76 (35:60:5 methanol/chloroform/water)

[α]$^{23}$$_D$: +160 (c=0.64 mathanol)

IR (KBr-Disk): υ(cm$^{-1}$)=3485 (OH), 3250 (amine) 2960 (CH$_3$), 2925 or 2855 (CH$_2$)

$^1$H NMR (300 MHz, 1:2 CD$_3$OD/CHCl$_3$)

δ=5.73 (d, 1H, J$_{1,5a}$=1.8 Hz, 5a-H), 4.16 (d, 1H, J$_{3,4}$=4.2 Hz, 4-H), 4.16 (br s, 2H, 6,6-H), 3.64 (dd, 1H, J$_{1,2}$=8.1 Hz, J$_{2,3}$=10.0 Hz, 2-H), 3.48 (dd, 1H, 3-H), 3.12 (dd, 1H, 1-H), 2.78 (ddd, 1H, J$_{1'a,2'}$=7.4 Hz, J$_{gem}$=111.2 Hz) and 2.57 (ddd, 1H) (NCH$_2$), 1.64-1.21 (m, 12H, 6×CH$_2$), 0.89 (t, 3H, J=6.7 Hz, CH$_2$CH$_3$).

Elementary Analysis

Calculated value C$_{15}$H$_{29}$NO$_4$: C, 62.69; H, 10.17; N, 4.87.

Actual value: C, 62.67; H, 10.47; N, 5.01.

<2> Measurement of Galactosidase Inhibitory Activity of the Substance of the Present Invention Knockout mouse skin fibroblast introduced with a human normal β-galactosidase (GP8) cDNA (*Biochem. Biophys. Res. Commun.*, 157(1), 238-244, 1988) and immortalized with an SV40 viral gene were cultured at 37° C. in an atmosphere of 5% CO$_2$, using Dulbecco's modified Eagle's medium (to be referred to as "DMEM" hereinafter: manufactured by Gibco) containing 10% fetal calf serum (to be referred to as "FCS" hereinafter), and when the cells became 80% confluent, the medium was exchanged with FCS-free DMEM containing 10 mM of NH$_4$Cl. After culturing for 24 hours, the supernatant was recovered and dialyzed against 10 mM phosphate buffer (pH=6.5) for 4 hours. Thereafter, the mixture was concentrated using VIVAPORE-20 (manufactured by Vivapore) and used as the enzyme source. Using 4-methylumbelliferyl-β-D-galactopyranoside as the fluorescent substrate, the enzyme activity during 30 minutes was measured in the presence or absence of the substance to be tested (Table 1). Final concentration of the substance 18 of the present invention was adjusted to 0.05, 0.125, 0.25, 0.5, 1, 2.5 or 5 μM.

TABLE 1

| Concentration of the substance 18 of the present invention (umol/L) | β-galactosidase activity (%) |
|---|---|
| 0.000 | 100.00 |
| 0.050 | 76.98 |
| 0.125 | 59.45 |
| 0.250 | 43.36 |
| 0.500 | 35.74 |
| 1.000 | 36.00 |
| 2.500 | 18.74 |
| 5.000 | 14.39 |

<3> Measurement of Mutant β-Galactosidase Activity

Cultured skin fibroblasts of a β-galactosidase-deficient knockout mouse was immortalized by introducing an SV40 viral gene, and enzyme genes integrated into pSV2neo and an expression vector were also introduced simultaneously, thereby establishing a model cell (*Brain Dev.*, 23(5), 284-287, 2001). The genes used are human normal (GP8) and mutant β-galactosidase gene Y316C, G123R (infantile G$_{M1}$-gangliosidosis), R201C (juvenile G$_{M1}$-gangliosidosis), I51T, T82M, R201H, R263S, R457Q (adult G$_{M1}$-gangliosidosis), W273L, Y83H, R482H and R482C (Morquio-B disease) (*Hum. Genet.*, 93(2), 109-114, 1994).

As a control substance, 0.5 mM N-(n-butyl)-deoxygalactonojirimycin (NB-DGJ: *The Journal of Biological Chemistry*, 269, 27108-27114 (1994)) was used, and the substance 18 of the present invention was used in an amount of 0.2 μM.

Specifically, after culturing the model cell for 4 days using a cell culture medium (10% FCS DMEM) containing the substance 18 of the present invention, the resulting cells were recovered and diluted such that the amount of protein in the suspension became a predetermined level, and then enzyme activity in the diluted suspension was measured. Using 4-methylumbelliferyl-β-D-galactopyranoside as the fluorescent substrate, the enzyme activity during 30 minutes was measured at 37° C. (Table 2). As a result, increase in the enzyme activity was observed by the genes excluding T82M, the enzyme activity was increased to 150% or more against the loss of enzyme activity by the mutation of R201C, R201H, R457Q, W273L, Y83H and the like genes, in comparison with the control, and a high activity was found by the substance 18 of the present invention in each case, so that a result indicating its usefulness particularly as a medicament was obtained.

TABLE 2

| Transferred genes | Control | Substance 18 of the present invention | Relative ratio (×100%) |
|---|---|---|---|
| GP8 | 74.94 | 78.87 | 1.05 |
| Y316C | 0.23 | 0.80 | 3.44 |
| G123R | 0.13 | 0.20 | 1.55 |
| R201C | 20.16 | 48.88 | 2.43 |
| I51T | 1.42 | 4.37 | 3.08 |
| R201H | 19.28 | 86.05 | 4.46 |
| T82M | 0.67 | 0.59 | 0.88 |
| P263S | 0.02 | 0.12 | 6.58 |
| R457Q | 5.84 | 14.17 | 2.42 |
| W273L | 11.83 | 17.71 | 1.50 |
| Y83H | 8.89 | 20.16 | 2.27 |
| R482H | 0.50 | 1.24 | 2.50 |
| R482C | 0.14 | 0.62 | 4.25 |

<4> Effects of the Substance 18 of the Present Invention on the Tissue Migration and Recovery of Enzyme Activity An administration test was carried out for 1 week using mice in order to verify that, when the drug of the present invention is orally administered, its active ingredient migrates into tissues and thereby shows its effect to recover β-galactosidase activity.

That is, tap water containing 1 mM (about 0.28 mg/ml) of the substance 18 of the present invention was continuously administered for 1 week as drinking water to recombinant mice (3 month-old) prepared by transferring a human mutant β-galactosidase gene R201C into β-galactosidase deficient knockout mice. One week thereafter, the mice were sacrificed to excise the cerebrum, the cerebellum, the heart, the lungs, the liver, the spleen, the kidney, a muscle (femoral muscle) and plasma. Also, tail tissues were used for the purpose of verifying changes in the β-galactosidase activity in the same individual before and after the administration. Each organ was crushed under ice-cooling using a homogenizer, and then the suspension of crushed cells was centrifuged at 8,000×g for 30 minutes. Thereafter, the supernatant fraction was recovered and used as an enzyme solution. The amount of protein in this enzyme solution was measured by the Bradford method, and the β-galactosidase activity was measured. With regard to the measurement of β-galactosidase activity, the enzyme activity during 30 minutes was measured at 37° C. using 4-methylumbelliferyl-β-D-galactopyranoside as the fluorogenic substrate. The aforementioned recombinant mice fed for 1 week using tap water free from the substance 18 of the present invention were used as respective controls, and, in order to examine changes in the enzyme activity in the same individual before and after feeding, their tails were used (negative control) similar to the case of the test groups. Three animals were used in each group to calculate the mean value. In this connection, since every mouse in the test group drank about 5 ml of the drinking water per day, it is calculated that about 1.4 mg per day, or about 10.2 mg per week, of the active ingredient (substance 18 of the present invention) was orally taken.

As a result, while changes in the β-galactosidase activity in the same individual before and after the feeding were not found in the negative control (Table 3: tails (non administration group)), it was found that the β-galactosidase activity in the test group was recovered close to 8 times in the same individual before and after the feeding (Table 3: tails (administration group)).

Diseases caused by the mutation of β-galactosidase are induced by the accumulation of substances to be degraded and metabolized naturally by β-galactosidase, and about the level of the activity obtained in the cerebrum and the cerebellum (about 50 nmol/mg protein/30 minutes) can fully alleviate symptoms of the diseases and prevent their onset.

In addition, it was found that the β-galactosidase activity in each organ was sharply improved in the test group, which was 4.7 times in the liver where improvement of the β-galactosidase activity was most low and 17.1 times in the spleen which showed the highest improvement. It was found that the β-galactosidase activity was improved 9.1 times in average in the test group. Particularly, since high β-galactosidase activity improving effect was obtained in the cerebrum and the cerebellum too, it was shown that the drug of the present invention is markedly useful as an agent for treating central nervous system. In this connection, since mortal case of the mice was not found in every test group and their health condition was markedly good throughout the testing period, it was suggested that the substance 18 of the present invention has high safety for the living body.

TABLE 3

|  | Control (nmol/mg protein/30 minutes) | Test group | Improving degree (Times) |
|---|---|---|---|
| Cerebrum | 8.4 | 50.5 | 6.0 |
| Cerebellum | 10.5 | 55.4 | 5.3 |
| Heart | 17.1 | 241.2 | 14.2 |
| Lungs | 8.0 | 98.9 | 12.4 |
| Liver | 39.7 | 186.8 | 4.7 |
| Spleen | 15.6 | 266.2 | 17.1 |
| Kidney | 27.8 | 171.1 | 6.2 |
| Muscle (femoral muscle) | 8.1 | 91.4 | 11.3 |
| Plasma | 2.9 | 23.0 | 7.9 |

|  | Before feeding | After feeding | Improving degree |
|---|---|---|---|
| Tail (administered group) | 78.0 | 518.8 | 6.7 |
| Tail (non-administered group) | 91.7 | 92.0 | 1.0 |

5> β-Glucosidase Inhibitory Activity of the Active Ingredient of the Drug 2 of the Present Invention The carba-sugar amine derivatives wherein n in the formula (24) is 5 and 7 were synthesized in accordance with the method described in *Bioorganic and Medicinal Chemistry Letters,* 6(8), 929-932 (1996) and used as the substances to be tested. In the following, the substance of n=5 is described as a substance (5) to be tested, and the substance of n=7 as a substance (7) to be tested.

Human fibroblasts derived from a healthy person was cultured at 37° C. under an atmosphere of 5% $CO_2$ using DMEM containing antibiotics (streptomycin and penicillin) and 10% FCS. When the cells became 80% confluent, they were recovered, and the recovered cells were crushed by an ultrasonic treatment and centrifuged at 12,000×g to obtain a supernatant.

Figure 1:
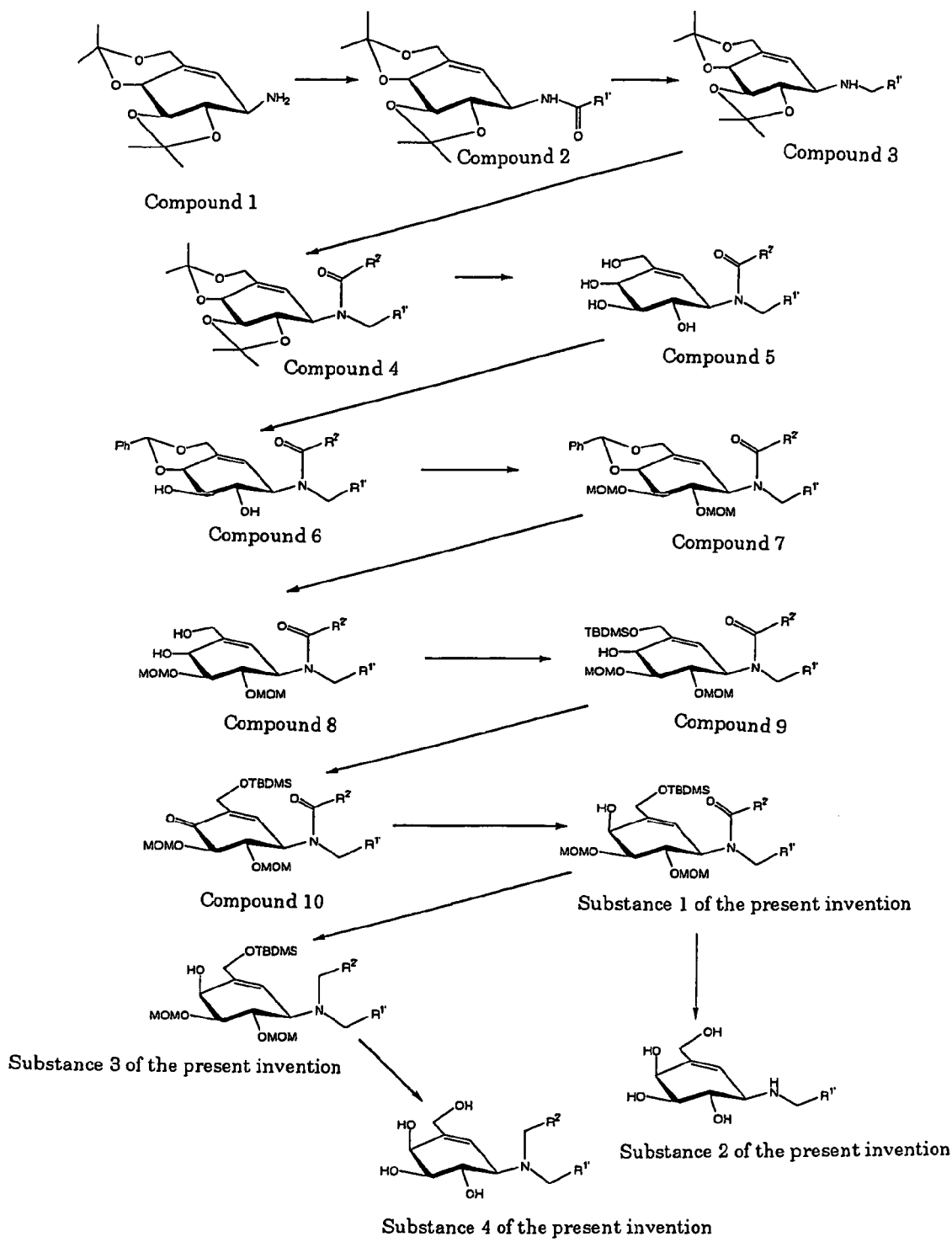
FIG. 1 is a graph shows a general synthesis scheme of substances 1 to 4 of the present invention.
Figure 2:
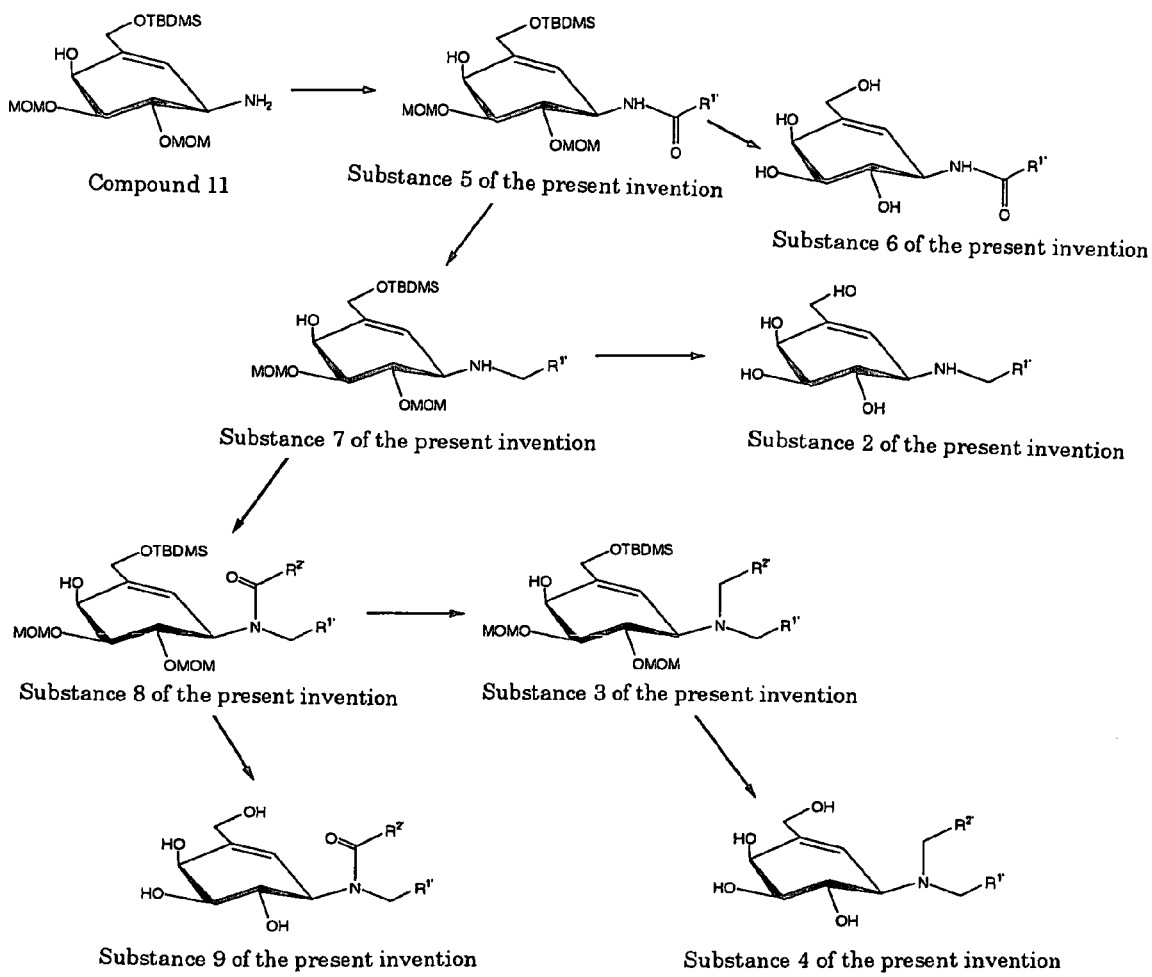
FIG. 2 shows a general synthesis scheme of substances 2 to 9 of the present invention.
Figure 3:
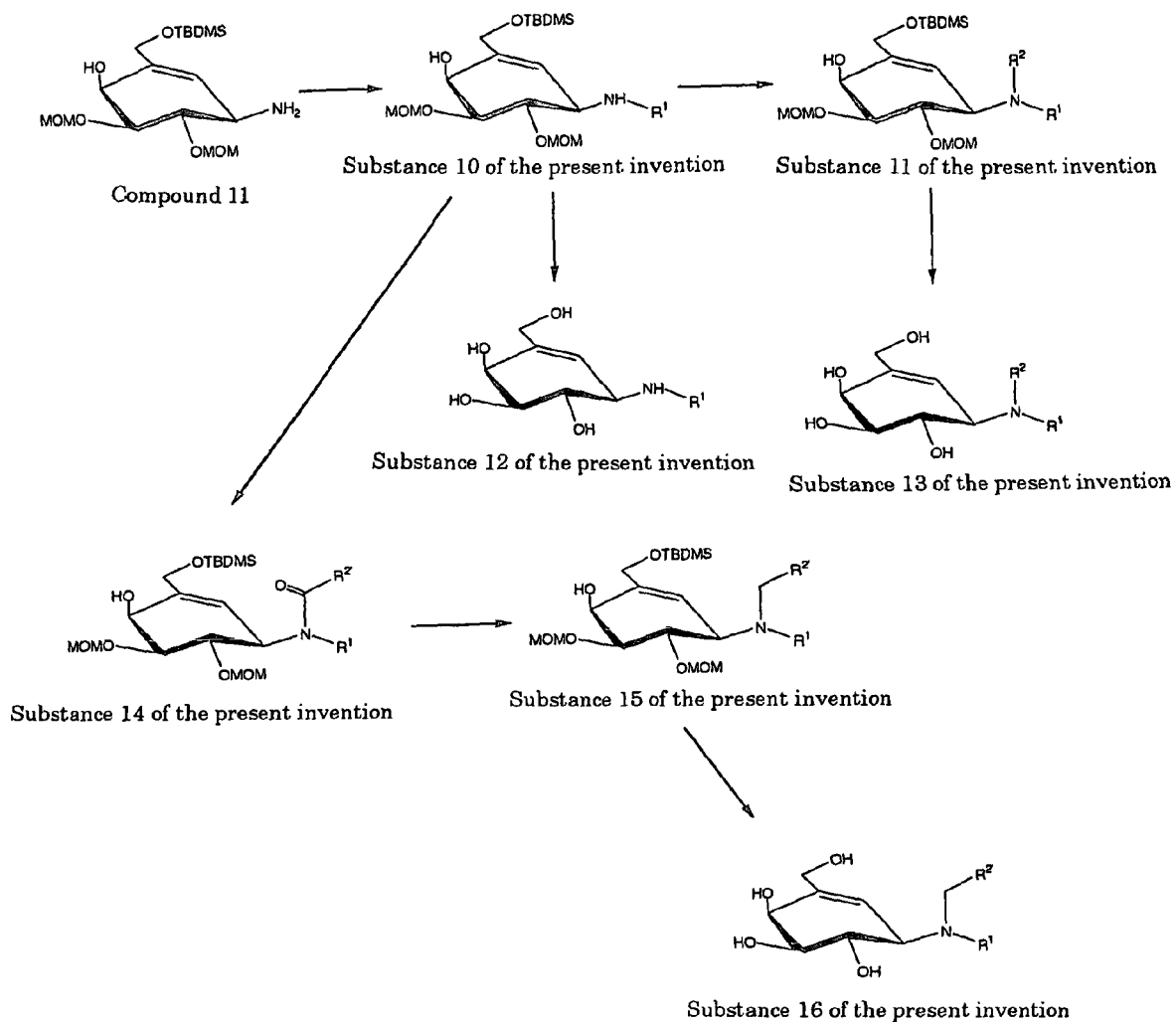
FIG. 3 shows a general synthesis scheme of substances 10 to 16 of the present invention.
Figure 4:
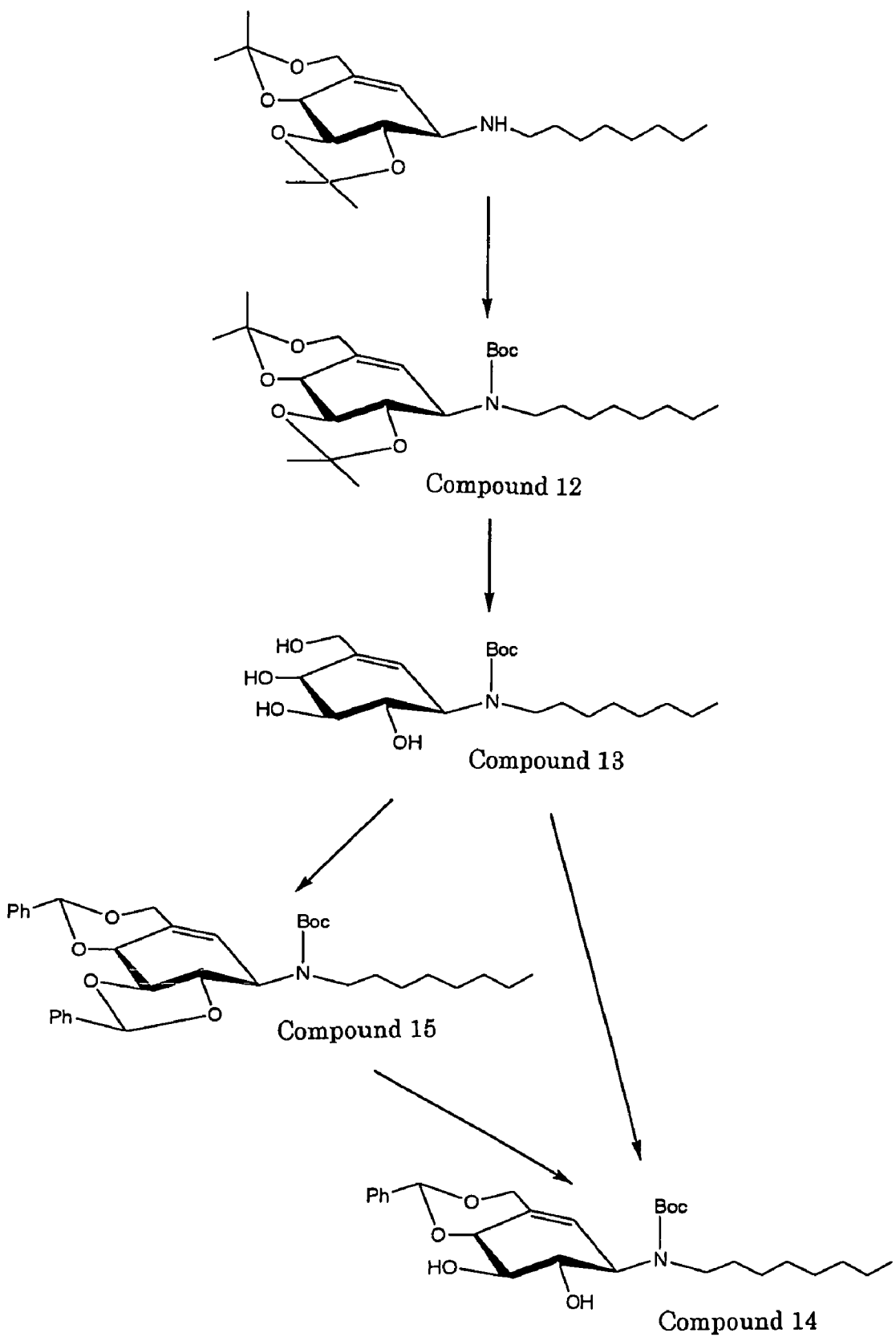
FIG. 4 shows a synthesis scheme of a compound 14 which is a synthesis intermediate of substance 18 of the present invention.
Figure 5:
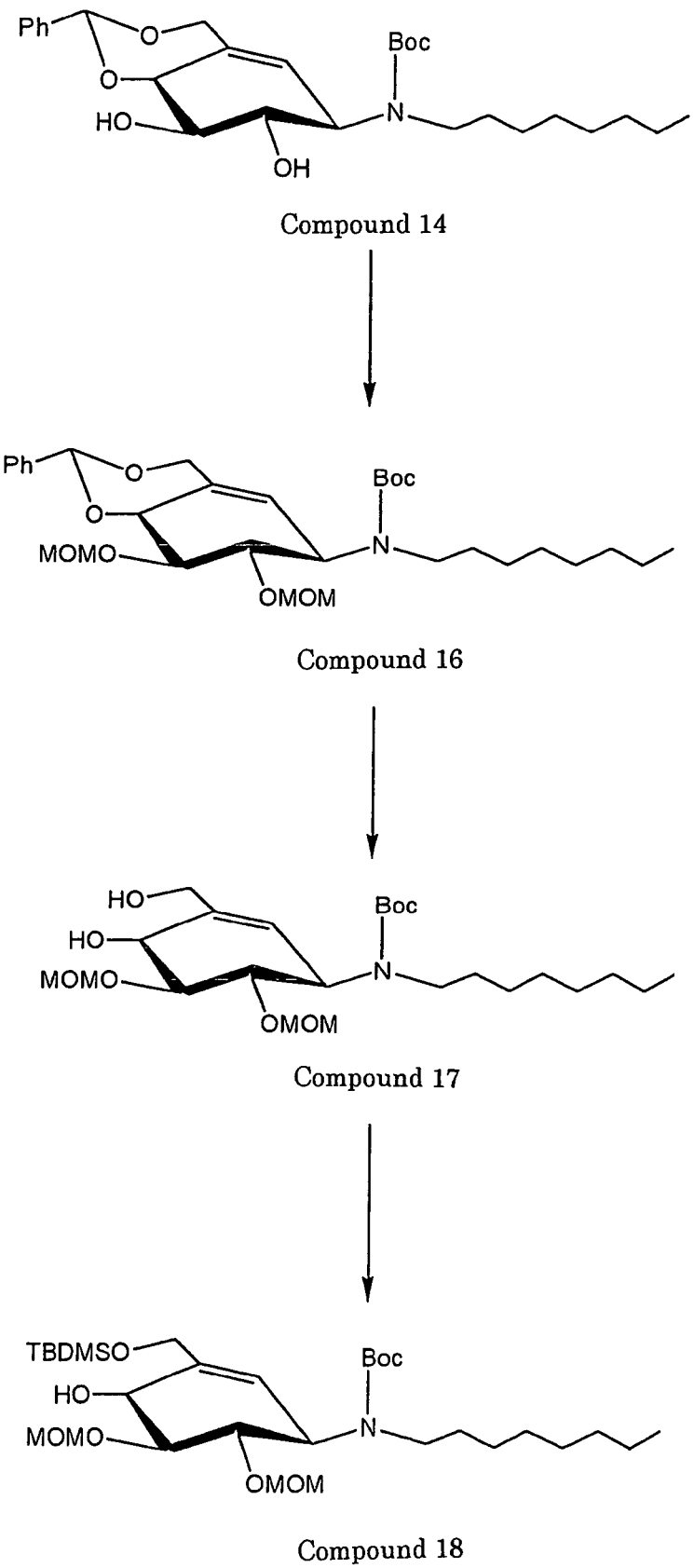
FIG. 5 shows a scheme for synthesizing a compound 18 which is a synthesis intermediate of substance 18 of the present invention from the compound 14.
Figure 6:
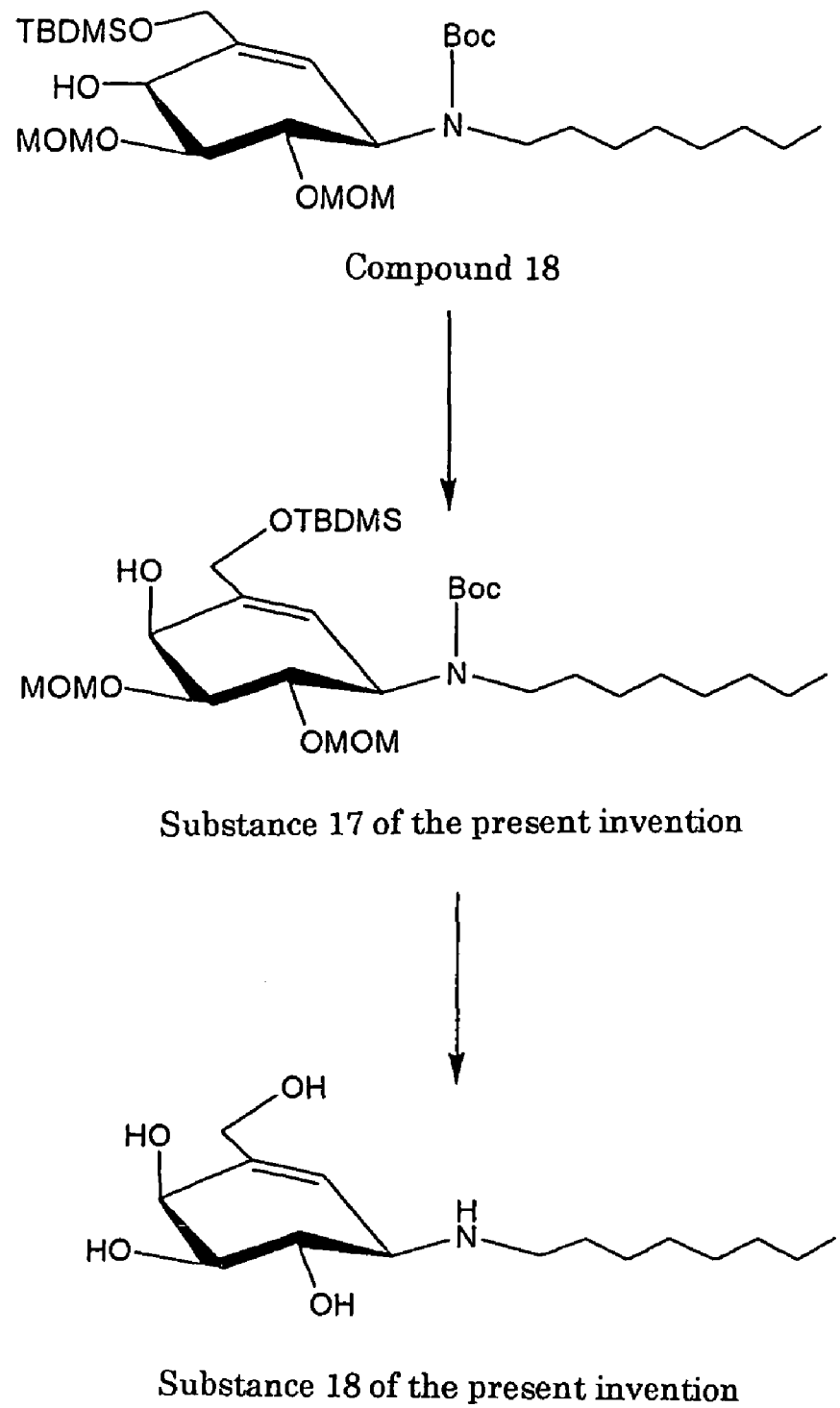
FIG. 6 shows a scheme for synthesizing substances 17 and 18 of the present invention from the compound 18.
Figure 7:
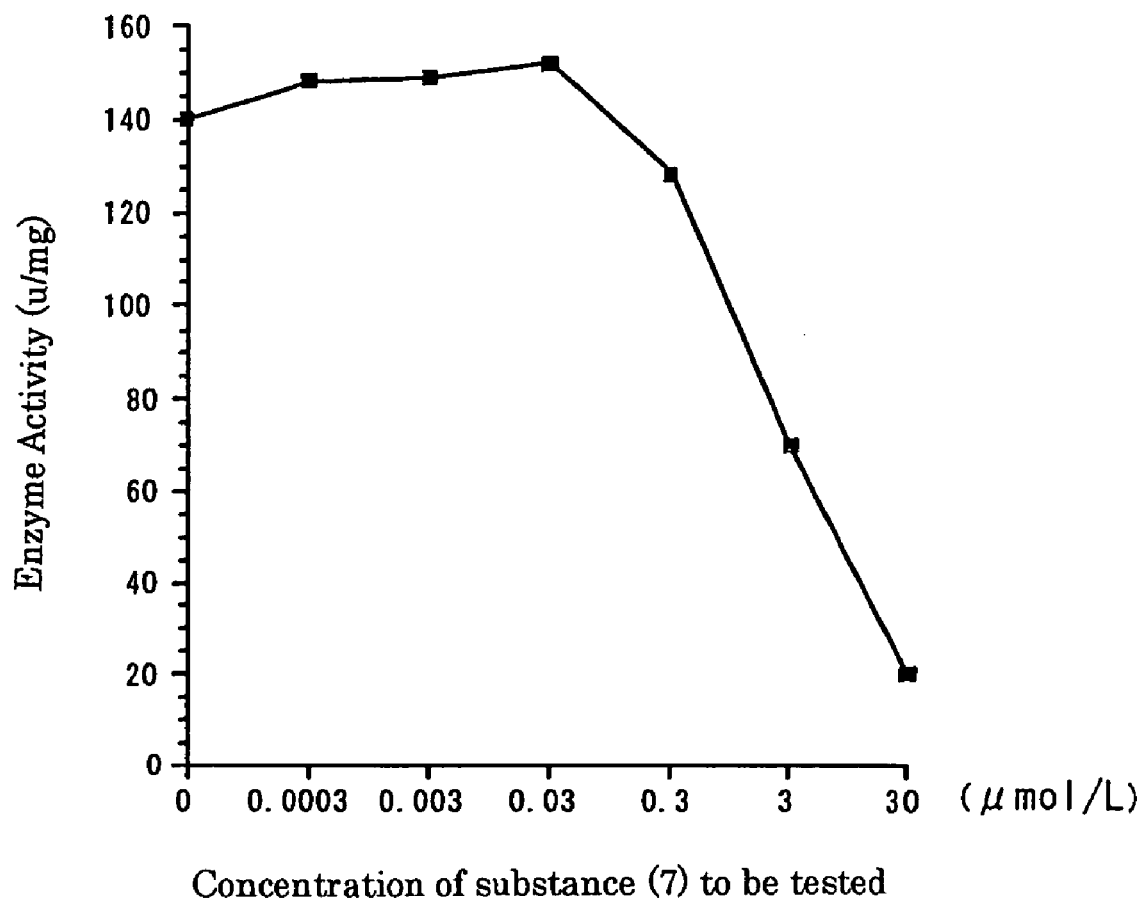
FIG. 7 is a graph showing action of a carba-sugar amine derivative (substance (7) to be tested) to inhibit activity of healthy human fibroblast β-glucocerebrosidase.
Figure 8:
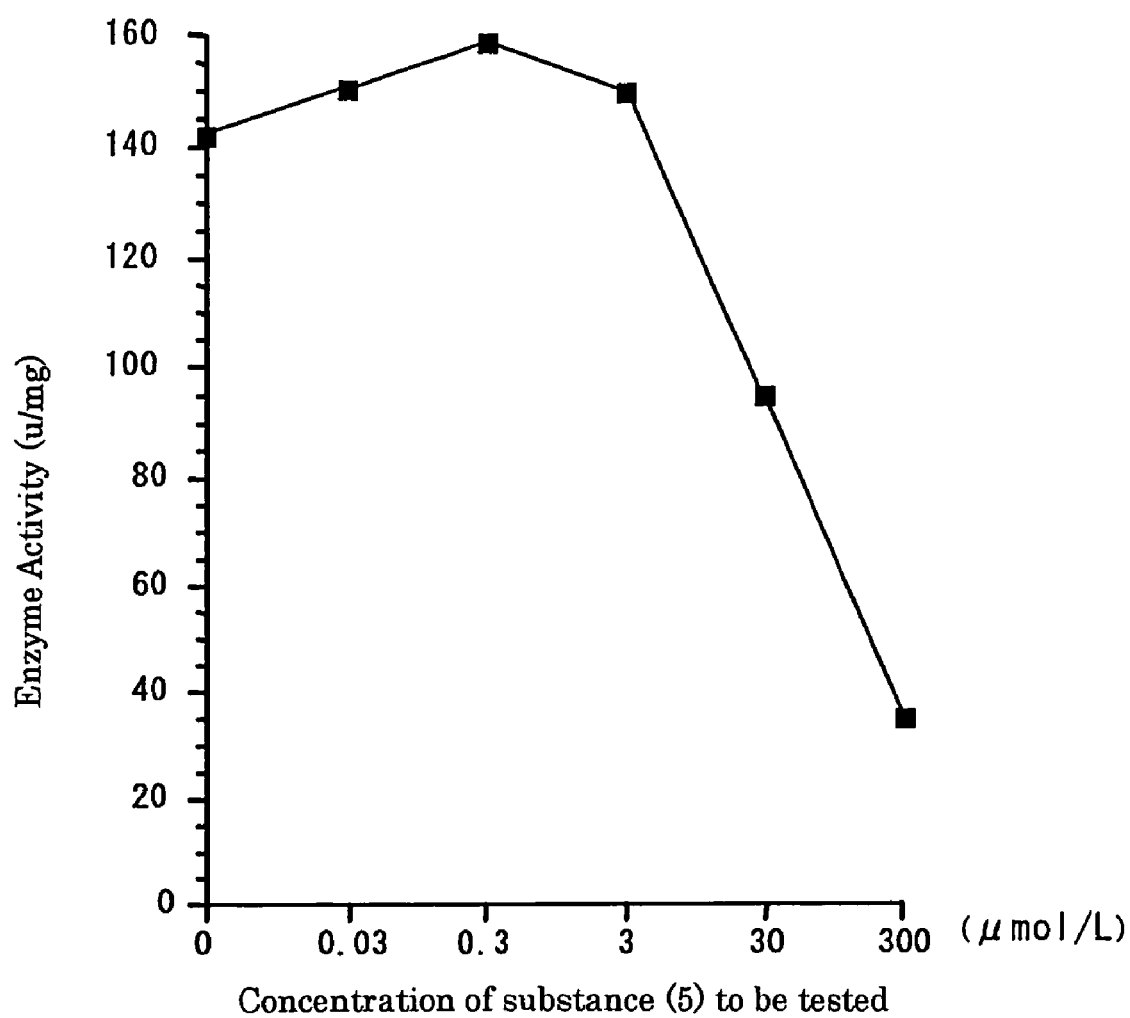
FIG. 8 is a graph showing action of a carba-sugar amine derivative (substance (5) to be tested) to inhibit activity of healthy human fibroblast β-glucocerebrosidase.

4-Methylumbelliferyl-β-D-glucopyranoside (0.1 M citrate buffer, pH 4.5) was added to the supernatant to give a concentration of 2 mM, and the enzyme activity was measured at 37° C. for 60 minutes in the absence of the substance (7) or (5) to be tested or in the presence of 0.0003, 0.003, 0.03, 0.3, 3 or 30 µM of the substance (7) or 0.03, 0.3, 3, 30 or 300 µM of the substance (5) to be tested. Released amount of 4-methylumbelliferone per 1 mg protein after 1 hour of incubation at 37° C. was defined as one unit of the enzyme activity (FIG. 7 and FIG. 8).

4-Methylumbelliferyl-β-D-glucopyranoside becomes a substrate of β-glucosidase including β-glucocerebrosidase (β-glucocerebrosidase is a species of the β-glucosidase). It was found that 0.3, 3 and 30 µM of the substance (7) or 3, 30 and 300 µM of the substance (5) to be tested markedly inhibits the β-glucosidase activity.

<6> Influence of the Active Ingredient of Drug 2 (Substance (7)) of the Present Invention Upon the Recovery of β-glucosidase Activity A substance to be tested was added to a culture medium, and its influence upon glucocerebrosidase activity was examined by culturing human fibroblasts (derived from healthy parson and Gaucher's disease patient) for 4 days. As the control, the culturing was carried out in the same manner using the medium to which the substance to be tested was not added. As the cells derived from Gaucher's disease patient, cells having respective genotypes of F213I/F213I, F213I/L444P, L444P/L444P, N370S/84GG and L444P/RecNciI (L444P+A456P+V460V) were used.

Figure 9:
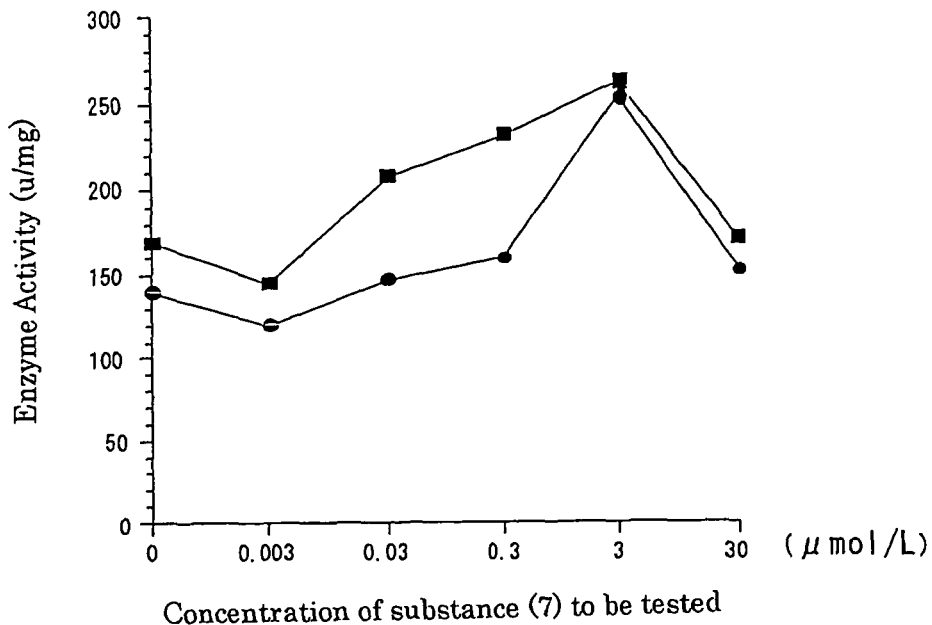
FIG. 9 is a graph showing changes in the β-glucocerebrosidase activity in two kinds of healthy human (derived from two healthy persons) fibroblast cultures in the presence of a carba-sugar amine derivative.
Figure 10:
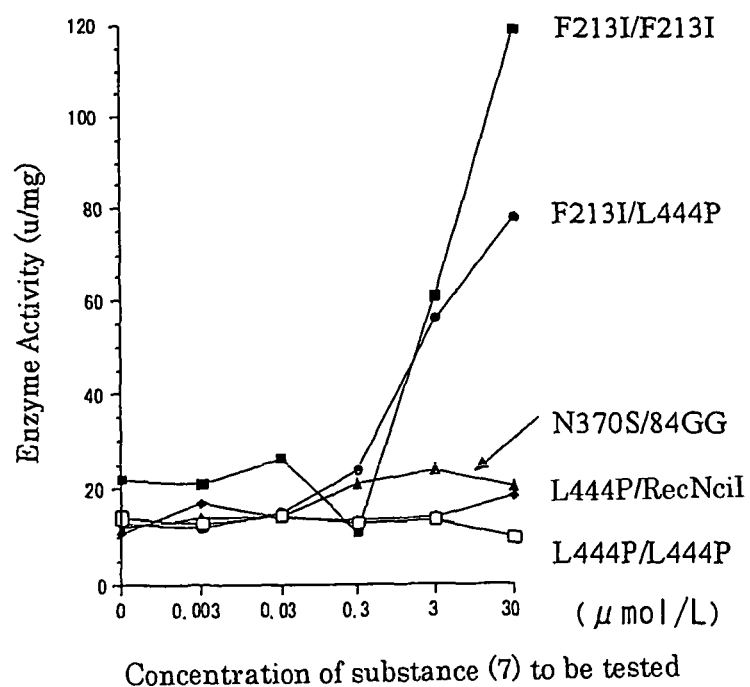
FIG. 10 is a graph showing changes in the β-glucocerebrosidase activity in Gaucher's disease patient-derived fibroblast in the presence of a carba-sugar amine derivative. Closed square shows a fibroblast of a genotype F213I/F213I, closed circle shows a fibroblast of a genotype F213I/L444P, closed triangle shows a fibroblast of a genotype N370S/

That is, the aforementioned cells were cultured for 4 days in DMEM (containing 10% FCS) which does not contain the substance (7) to be tested or DMEM (containing 10% FCS) containing 0.003, 0.03, 0.3, 3 or 30 µM of the substance (7) to be tested, and then the resulting cells were recovered. The thus recovered cells were homogenized by an ultrasonic treatment and centrifuged at 12,000×g to obtain a supernatant, and the enzyme activity of this supernatant was measured. The enzyme activity was measured at 37° C. for 60 minutes with the use of 4-methylumbelliferyl-β-D-glucopyranoside (0.1 M citrate buffer, pH 4.5). Released amount of 4-methylumbelliferone per 1 mg protein after 1 hour of incubation at 37° C. was defined as one unit of the enzyme activity (fibroblasts derived from healthy persons: FIG. 9, fibroblasts derived from Gaucher's disease patients, FIG. 10, comparison of fibroblasts derived from healthy persons with fibroblasts derived from Gaucher's disease patients (F213I/F213I, F213I/L444P) when 30 µM of the substance (7) to be tested was added: FIG. 11).

As a result, 30 µM of the substance (7) to be tested considerably increased the β-glucosidase activity in cells of F213I/F213I and F213I/L444P among the fibroblasts derived from Gaucher's disease patients. This result suggests that the substance (7) to be tested is concerned in the recovery of the activity of glucocerebrosidase having F213I mutation or improvement of the gene expression.

<7> Influence of Substance (7) to be Tested Upon the Expression of Glucocerebrosidase Gene In order to examine whether or not the substance (7) to be tested is concerned in the reinforcement of the expression of the glucocerebrosidase gene having F213I mutation, expression of the glucocerebrosidase gene in a fibroblast derived from a Gaucher's disease patient having a genotype of F213I/F213I was observed.

That is, fibroblasts derived from a healthy person or fibroblasts derived from a Gaucher's disease patient which has above-described genotype was cultured for 4 days in DMEM (containing 10% FCS) which does not contain the substance (7) to be tested or DMEM (containing 10% FCS) containing 30 μM of the substance (7) to be tested, and then total RNA was extracted with acidic guanidinothiocyanate-phenol-chloroform and total amount of β-glucosidase mRNA was measured by a competitive RT-PCR method using a human β-actin competitive PCR set (manufactured by Promega). In the human β-actin competitive PCR set, a β-glucosidase cDNA fragment as a product of reverse transcription (SEQ ID NO:1) was used as a primer, and the primer described in SEQ ID NO:2 as a competitive primer (FIG. 12).

Since it is apparent from the result that similar degree of the transcription of β-glucocerebrosidase gene is occurring in both of the fibroblasts derived from a healthy person and fibroblast derived from a Gaucher's disease patient without depending on the presence or absence of the substance (7) to be tested, it was suggested that the substance to be tested does not act upon the gene transcription.

<8> Verification of the Expressed Amount of β-Glucocerebrosidase by Western Blotting Analysis In order to observe an expressed amount of the enzyme protein of β-glucocerebrosidase in respective cells used in <6>, Western blotting analysis was carried out.

That is, 20 μg of protein was separated by 10% sodium dodecyl sulfate-polyacrylamide gel electrophoresis (SDS-PAGE) from a supernatant obtained by 4 days of culturing carried out in the same manner as in Example 2 using DMEM which does not contain the substance (7) to be tested or DMEM containing 20 μM of the substance (7) to be tested, and transferred on a nitrocellulose membrane at 100 V for 1 hour. Thereafter, the nitrocellulose membrane was incubated using an anti-human β-glucocerebrosidase mouse monoclonal antibody (8E4: obtained from professor Eto at The Jikei University School of Medicine: used by diluting 500 times) as the primary antibody, labeled with a horseradish peroxidase-labeled anti-mouse IgG antibody as the secondary antibody, and then visualized using tetramethylbenzidine as the substrate (FIG. 13).

As a result, it was indicated that the substance (7) to be tested increases the enzyme protein of β-glucocerebrosidase which can be detected by the anti-human β-glucocerebrosidase antibody, in the fibroblasts derived from a Gaucher's disease patient having a genotype of F213I/F213I. Increase in the enzyme protein of β-glucocerebrosidase was also found in fibroblasts derived from a healthy person and a patient having a genotype of N370S/88GG.

In addition, a fibroblast derived from a Gaucher disease patient having a genotype of F213I/F213I was cultured for 4 days using DMEM which does not contain the substance (7) to be tested or DMEM containing 0.3, 3, 30 or 100 μM of the substance (7) to be tested, and the supernatant was recovered in the same manner as in <6> to carry out western blotting analysis in the same manner as described in the foregoing (FIG. 14).

As a result, it was indicated that the amount of the enzyme protein of β-glucocerebrosidase which can be detected by the anti-human β-glucocerebrosidase antibody is increased particularly when the cells are cultured using 3 or 30 μM of the substance (7) to be tested.

<9> Influence of the Substance (7) to be Tested Upon the Stability of β-Glucocerebrosidase Influence of the substance (7) to be tested upon the stability of mutated β-glucocerebrosidase was examined.

That is, a fibroblast derived from a Gaucher's disease patient having a genotype of F213I/F213I was cultured for 4 days in DMEM containing 10% FCS, and the supernatant was recovered in the same manner as in <5>. Under conditions of not adding the substance (7) to be tested, this was kept at 37° C. for 20, 40 or 60 minutes in 0.1 M citrate-phosphate buffer of pH 5, 6 or 7, and then mixed with three volumes of 0.2 M citrate-phosphate buffer (pH 4.5) and pre-incubated under ice-cooling. Thereafter, the enzyme activity was measured using 4-methylumbelliferyl-β-D-glucopyranoside as the substrate (FIG. 15).

As a result, it was found that the stability of this β-glucosidase at pH 7 was extremely low in comparison with the case of pH 5 and 6.

Next, the aforementioned supernatant was adjusted to pH 7 in 0.1 M citrate-phosphate buffer containing 0.1, 1 or 10 μM of the substance (7) to be tested and kept at 37° C. for 20, 40 or 60 minutes in the same manner, and then the enzyme activity was measured in the same manner as described in the foregoing (FIG. 16).

As a result, it was found that the substance (7) to be tested improves stability of the β-glucosidase which is unstable at pH 7.

<10> Relationship Between the Substance (7) to be Tested and Glucocerebroside

In order to examine effect of the substance (7) to be tested on the metabolism of glucocerebroside, determination of radioactivity-labeled glucocerebroside was carried out.

That is, a fibroblast derived from healthy person or a Gaucher's disease patient was cultured for one week using a culture medium which does not contain serine and then cultured for three days using a culture medium containing $^{14}$C-serine (pulse). Thereafter, this was further cultured for 5 days in DMEM (containing 10% DMEM) which does not contain the substance (7) to be tested or DMEM (containing 10% FCS) containing the substance (7) to be tested (30 μM) (chase).

After washing the cells three times with PBS, neutral glycolipid was extracted with a mixed solvent of chloroform:methanol (1:2) and subjected to a weak alkali treatment. Thin layer chromatography was carried out using a mixed solvent of chloroform:methanol:water (55:25:4) as the developing solvent. The band of glucocerebroside was detected (FIG. 17) and determined (FIG. 18). An imaging system (Fuji-BAS2500: manufactured by Fuji Photo Film) was used for the detection and determination.

As a result, it was found that the substance (7) to be tested reduces the amount of glucocerebroside as the substrate of β-glucocerebrosidase to its normal cellular level.

<11> Influence of the Substance (7) to be Tested Upon Distribution of β-Glucocerebrosidase Effect of the substance (7) to be tested was examined regarding the accumulation of β-glucocerebrosidase into lysosome in fibroblasts derived from a Gaucher's disease patient having F213I mutation.

That is, fibroblasts derived from a Gaucher's disease patient was cultured for 4 days in DMEM (containing 10% FCS) to which the substance (7) to be tested (30 μM) was added or in un-added DMEM. The medium was exchanged with DMEM (containing 10% FCS), and the culturing was carried out at 37° C. for 1 hour in the presence of a lysosome marker (Lyso Tracker Red: manufactured by Molecular Probe Co., Ltd.). Thereafter, the cells were fixed with 4% p-formaldehyde and treated with methanol. The fixed cells were incubated with the aforementioned primary antibody of anti-glucocerebroside β-glucosidase monoclonal antibody 8E4, and then visualized using an anti-mouse IgG Alexa 488 as the secondary antibody. β-Glucocerebrosidase is detected by a green fluorescence, and lysosome emits a red fluorescence.

When imaging was carried out using a confocal microscope, while the mutant cell lysosome was detected by a red fluorescence due to reduced β-glucocerebrosidase, the group of cells to which the substance (7) to be tested was added was detected by a yellow fluorescence (yellow color is developed when a light source region of red is overlapped with a light source region of green), so that it was revealed that β-glucocerebrosidase was increased in the lysosome thereof.

The result shows that the unstable mutant enzyme protein was stabilized by the addition of the substance (7) to be tested, and the β-glucocerebrosidase was efficiently transferred into lysosome which is a cell organelle where the enzyme originally functions.

INDUSTRIAL APPLICABILITY

A novel glycolipid metabolic disorder treating agent and a novel pseudo-sugar having β-galactosidase inhibitory activity are provided by the present invention.

The invention claimed is:

1. A carba-sugar amine compound represented by the following formula (1):

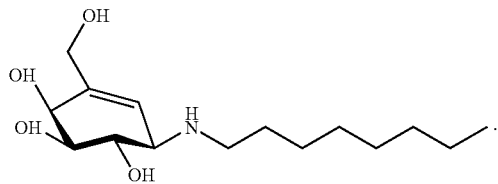

2. An agent for treating a glycolipid metabolic disorder selected from the group consisting of $G_{m1}$ gangliosidosis, Morquio-B disease and Krabbe's disease, which comprises the carba-sugar amine compound according to claim 1 as an active ingredient.

3. The agent for treating a glycolipid metabolic disorder according to claim 2, which is a preparation for oral administration.

4. A method for stabilizing β-galactosidase comprising administering to a subject in need thereof an effective amount of a composition comprising the carba-sugar amine compound according to claim 1 as an active ingredient.

5. A method for treating a glycolipid metabolic disorder selected from the group consisting of $G_{m1}$ gangliosidosis, Morquio-B disease, and Krabbe's disease, comprising administering to a subject in need thereof an effective amount of the carba-sugar amine compound according to claim 1.

6. The method according to claim 5, wherein the carba-sugar amine compound is orally administered.

7. A method for regenerating the activity of β-galactosidase reduced or lost due to a mutation in the living body, comprising administering to a subject in need thereof an effective amount of the carba-sugar amine compound according to claim 1.

* * * * *